(12) United States Patent
Cohn et al.

(10) Patent No.: US 10,874,422 B2
(45) Date of Patent: Dec. 29, 2020

(54) SYSTEMS AND METHODS FOR INCREASING BLOOD FLOW

(71) Applicant: TVA Medical, Inc., Austin, TX (US)

(72) Inventors: William E. Cohn, Bellaire, TX (US);
Thomas D. Pate, Austin, TX (US);
Philip M. Tetzlaff, Austin, TX (US);
David Gunther, Duxbury, MA (US)

(73) Assignee: TVA Medical, Inc., Austin, TX (US)

( * ) Notice: Subject to any disclaimer, the term of this patent is extended or adjusted under 35 U.S.C. 154(b) by 0 days.

(21) Appl. No.: 15/406,743

(22) Filed: Jan. 15, 2017

(65) Prior Publication Data

US 2017/0202603 A1  Jul. 20, 2017

Related U.S. Application Data

(60) Provisional application No. 62/279,633, filed on Jan. 15, 2016, provisional application No. 62/399,473, (Continued)

(51) Int. Cl.
*A61F 2/07* (2013.01)
*A61B 17/00* (2006.01)
(Continued)

(52) U.S. Cl.
CPC .......... *A61B 17/32075* (2013.01); *A61F 2/82* (2013.01); *A61B 18/1492* (2013.01); *A61B 2017/00252* (2013.01); *A61B 2017/22097* (2013.01); *A61B 2018/00404* (2013.01); *A61B 2018/00601* (2013.01); *A61F 2/07* (2013.01); *A61F 2/2418* (2013.01)

(58) Field of Classification Search
CPC .... A61B 2017/00252; A61B 17/32075; A61B 2017/22097; A61B 2018/00404; A61B 2018/00601; A61B 17/11; A61B 2017/1103; A61B 2017/1107; A61B 2018/00345
See application file for complete search history.

(56) References Cited

U.S. PATENT DOCUMENTS 3,649,850 A  3/1972  Davis
3,827,436 A  8/1974  Stumpf et al.
(Continued)

FOREIGN PATENT DOCUMENTS

CA  2883209 A1  4/2014
CN  1730123 A   2/2006
(Continued)

OTHER PUBLICATIONS

Extended European Search Report for EP Application No. 17739123.2.
(Continued)

*Primary Examiner* — Katrina M Stransky
(74) *Attorney, Agent, or Firm* — Dinsmore & Shohl LLP

(57) ABSTRACT

Described here are devices, systems, and methods for improving blood flow in a vessel. Generally, the method may comprise advancing a catheter into a first vessel proximal to an occlusion in the first vessel and forming a fistula between the first vessel and a second vessel. This may deliver blood flow around an occlusion to ischemic tissues located in the peripheral vasculature.

21 Claims, 12 Drawing Sheets

Related U.S. Application Data filed on Sep. 25, 2016, provisional application No. 62/399,465, filed on Sep. 25, 2016.

(51) Int. Cl.
*A61B 17/22* (2006.01)
*A61B 18/00* (2006.01)
*A61B 18/14* (2006.01)
*A61B 17/3207* (2006.01)
*A61F 2/82* (2013.01)
*A61F 2/24* (2006.01)

(56) References Cited

U.S. PATENT DOCUMENTS

| | | |
|---|---|---|
| 4,416,664 A | 11/1983 | Womack |
| 4,802,475 A | 2/1989 | Weshahy |
| 5,313,943 A | 5/1994 | Houser et al. |
| 5,383,460 A | 1/1995 | Jang et al. |
| 5,697,909 A | 12/1997 | Eggers et al. |
| 5,782,239 A | 7/1998 | Webster, Jr. |
| 5,800,487 A | 9/1998 | Mikus et al. |
| 5,830,222 A | 11/1998 | Makower |
| 5,830,224 A | 11/1998 | Cohn et al. |
| 5,836,947 A | 11/1998 | Fleischman et al. |
| 5,895,404 A | 4/1999 | Ruiz |
| 5,971,979 A | 10/1999 | Joye et al. |
| 6,004,330 A | 12/1999 | Middleman et al. |
| 6,032,677 A | 3/2000 | Blechman et al. |
| 6,039,730 A | 3/2000 | Rabin et al. |
| 6,068,638 A | 5/2000 | Makower |
| 6,071,274 A | 6/2000 | Thompson et al. |
| 6,099,542 A | 8/2000 | Cohn et al. |
| 6,159,225 A | 12/2000 | Makower |
| 6,190,353 B1 | 2/2001 | Makower et al. |
| 6,197,025 B1 | 3/2001 | Grossi et al. |
| 6,217,575 B1 | 4/2001 | DeVore et al. |
| 6,231,587 B1 | 5/2001 | Makower |
| 6,256,525 B1 | 7/2001 | Yang et al. |
| 6,283,988 B1 | 9/2001 | Laufer et al. |
| 6,287,306 B1 | 9/2001 | Kroll et al. |
| 6,302,875 B1 | 10/2001 | Makower et al. |
| 6,327,505 B1 | 12/2001 | Medhkour et al. |
| 6,347,247 B1 | 2/2002 | Dev et al. |
| 6,355,029 B1 | 3/2002 | Joye et al. |
| 6,357,447 B1 | 3/2002 | Swanson et al. |
| 6,379,353 B1 | 4/2002 | Nichols |
| 6,383,180 B1 | 5/2002 | Lalonde et al. |
| 6,394,956 B1 | 5/2002 | Chandrasekaran et al. |
| 6,400,976 B1 | 6/2002 | Champeau |
| 6,428,534 B1 | 8/2002 | Joye et al. |
| 6,461,356 B1 | 10/2002 | Patterson |
| 6,464,665 B1 | 10/2002 | Heuser |
| 6,464,723 B1 | 10/2002 | Callol |
| 6,468,268 B1 | 10/2002 | Abboud et al. |
| 6,475,214 B1 | 11/2002 | Moaddeb |
| 6,475,226 B1 | 11/2002 | Belef et al. |
| 6,527,724 B1 | 3/2003 | Fenici |
| 6,527,769 B2 | 3/2003 | Langberg et al. |
| 6,542,766 B2 | 4/2003 | Hall et al. |
| 6,544,230 B1 | 4/2003 | Flaherty et al. |
| 6,569,158 B1 | 5/2003 | Abboud et al. |
| 6,569,162 B2 | 5/2003 | He |
| 6,579,311 B1 * | 6/2003 | Makower ............ A61B 1/3137 604/8 |
| 6,585,650 B1 | 7/2003 | Solem |
| 6,592,577 B2 | 7/2003 | Abboud et al. |
| 6,629,987 B1 | 10/2003 | Gambale et al. |
| 6,635,053 B1 | 10/2003 | Lalonde et al. |
| 6,655,386 B1 | 12/2003 | Makower et al. |
| 6,656,173 B1 | 12/2003 | Palermo |
| 6,663,625 B1 | 12/2003 | Ormsby et al. |
| 6,669,709 B1 | 12/2003 | Cohn et al. |
| 6,673,085 B1 | 1/2004 | Berg |
| 6,676,657 B2 | 1/2004 | Wood |
| 6,682,525 B2 | 1/2004 | Lalonde et al. |
| 6,695,878 B2 | 2/2004 | McGuckin, Jr. et al. |
| 6,709,444 B1 | 3/2004 | Makower |
| 6,719,756 B1 | 4/2004 | Muntermann |
| 6,726,697 B2 | 4/2004 | Nicholas et al. |
| 6,733,494 B2 | 5/2004 | Abboud et al. |
| 6,736,808 B1 | 5/2004 | Motamedi et al. |
| 6,761,708 B1 | 7/2004 | Chiu et al. |
| 6,761,714 B2 | 7/2004 | Abboud et al. |
| 6,780,181 B2 | 8/2004 | Kroll et al. |
| 6,849,073 B2 | 2/2005 | Hoey et al. |
| 6,855,143 B2 | 2/2005 | Davison et al. |
| 6,887,234 B2 | 5/2005 | Abboud et al. |
| 6,911,026 B1 | 6/2005 | Hall et al. |
| 6,932,814 B2 | 8/2005 | Wood |
| 6,936,024 B1 | 8/2005 | Houser |
| 6,960,209 B2 | 11/2005 | Clague et al. |
| 6,971,983 B1 | 12/2005 | Cancio |
| 6,981,972 B1 | 1/2006 | Farley et al. |
| 7,059,330 B1 | 6/2006 | Makower et al. |
| 7,060,063 B2 | 6/2006 | Marion et al. |
| 7,094,235 B2 | 8/2006 | Francischelli |
| 7,155,293 B2 | 12/2006 | Westlund et al. |
| 7,179,270 B2 | 2/2007 | Makower |
| 7,189,231 B2 | 3/2007 | Clague et al. |
| 7,214,234 B2 | 5/2007 | Rapacki et al. |
| 7,231,260 B2 | 6/2007 | Wallace et al. |
| 7,250,051 B2 | 7/2007 | Francischelli |
| 7,288,075 B2 | 10/2007 | Parihar et al. |
| 7,303,554 B2 | 12/2007 | Lalonde et al. |
| 7,306,598 B2 | 12/2007 | Truckai et al. |
| 7,335,198 B2 | 2/2008 | Eggers et al. |
| 7,341,063 B2 | 3/2008 | Garbibaldi et al. |
| 7,367,341 B2 | 5/2008 | Anderson et al. |
| 7,374,567 B2 | 5/2008 | Heuser |
| 7,387,636 B2 | 6/2008 | Cohn et al. |
| 7,407,506 B2 | 8/2008 | Makower |
| 7,522,950 B2 | 4/2009 | Fuimaono et al. |
| 7,628,768 B2 | 12/2009 | Faul et al. |
| 7,702,387 B2 | 4/2010 | Stevenson et al. |
| 7,727,268 B2 | 6/2010 | Cunniffe et al. |
| 7,744,596 B2 | 6/2010 | Young et al. |
| 7,811,281 B1 | 10/2010 | Rentrop |
| 7,828,814 B2 | 11/2010 | Brenneman et al. |
| 7,846,172 B2 | 12/2010 | Makower |
| 7,849,860 B2 | 12/2010 | Makower et al. |
| 7,857,809 B2 | 12/2010 | Drysen |
| 7,881,797 B2 | 2/2011 | Griffin et al. |
| 7,955,326 B2 | 6/2011 | Paul et al. |
| 7,967,769 B2 | 6/2011 | Faul et al. |
| 7,967,770 B2 | 6/2011 | Li et al. |
| 8,010,208 B2 | 8/2011 | Nimer et al. |
| 8,048,016 B2 | 11/2011 | Faul et al. |
| 8,052,680 B2 | 11/2011 | Hassett et al. |
| 8,062,321 B2 | 11/2011 | Heuser et al. |
| RE43,007 E | 12/2011 | Lalonde et al. |
| 8,075,555 B2 | 12/2011 | Truckai et al. |
| 8,088,171 B2 | 1/2012 | Brenneman |
| 8,100,899 B2 | 1/2012 | Doty et al. |
| 8,118,809 B2 | 2/2012 | Paul et al. |
| 8,135,467 B2 | 3/2012 | Markowitz et al. |
| 8,142,454 B2 | 3/2012 | Harrison et al. |
| 8,192,425 B2 | 6/2012 | Mirza et al. |
| 8,200,466 B2 | 6/2012 | Spilker et al. |
| 8,226,592 B2 | 7/2012 | Brenneman et al. |
| 8,231,618 B2 | 7/2012 | Viswanathan et al. |
| 8,236,014 B2 | 8/2012 | Brenneman et al. |
| 8,262,649 B2 | 9/2012 | Francischelli |
| 8,273,095 B2 | 9/2012 | Brenneman et al. |
| 8,328,797 B2 | 12/2012 | Wilson et al. |
| 8,333,758 B2 | 12/2012 | Joye et al. |
| 8,361,061 B2 | 1/2013 | Esch et al. |
| 8,366,707 B2 | 2/2013 | Kassab et al. |
| 8,382,697 B2 | 2/2013 | Brenneman et al. |
| 8,409,196 B2 | 4/2013 | Durgin et al. |
| 8,413,664 B2 | 4/2013 | Appling |
| 8,414,572 B2 | 4/2013 | Davison et al. |
| 8,419,681 B2 | 4/2013 | Sell |
| 8,439,909 B2 | 5/2013 | Wang et al. |

(56) References Cited

U.S. PATENT DOCUMENTS

| | | |
|---|---|---|
| 8,454,587 B2 | 6/2013 | Lalonde et al. |
| 8,475,441 B2 | 7/2013 | Babkin et al. |
| 8,486,062 B2 | 7/2013 | Belhe et al. |
| 8,486,064 B2 | 7/2013 | Van Wyk et al. |
| 8,551,032 B2 | 10/2013 | Faul et al. |
| 8,574,185 B2 | 11/2013 | Faul et al. |
| 8,585,700 B2 | 11/2013 | Katou |
| 8,608,754 B2 | 12/2013 | Wensel et al. |
| 8,641,724 B2 | 2/2014 | Brenneman et al. |
| 8,649,879 B2 | 2/2014 | DiGiore et al. |
| 8,676,309 B2 | 3/2014 | Deem et al. |
| 8,685,014 B2 | 4/2014 | Babkin et al. |
| 8,700,179 B2 | 4/2014 | Pianca et al. |
| 8,715,281 B2 | 5/2014 | Barlow et al. |
| 8,758,334 B2 | 6/2014 | Coe et al. |
| 8,771,267 B2 | 7/2014 | Kunis et al. |
| 8,784,409 B2 | 7/2014 | Robilotto et al. |
| 8,790,341 B2 | 7/2014 | Pappone et al. |
| 8,876,699 B2 | 11/2014 | Sato et al. |
| 8,876,815 B2 | 11/2014 | Coe et al. |
| 8,882,765 B2 | 11/2014 | Kassab et al. |
| 8,911,435 B2 | 12/2014 | Katoh et al. |
| 8,951,251 B2 | 2/2015 | Willard |
| 9,017,323 B2 | 4/2015 | Miller et al. |
| 9,039,702 B2 | 5/2015 | Miller et al. |
| 9,072,880 B2 | 7/2015 | Phillips et al. |
| 9,089,316 B2 | 7/2015 | Baust et al. |
| 9,108,018 B2 | 8/2015 | Dickinson et al. |
| 9,155,827 B2 | 10/2015 | Franano |
| 9,204,916 B2 | 12/2015 | Lalonde |
| 9,259,340 B2 | 2/2016 | Heuser et al. |
| 9,283,034 B2 | 3/2016 | Katoh et al. |
| 9,307,992 B2 | 4/2016 | Wilson et al. |
| 9,314,329 B2 | 4/2016 | Dickinson et al. |
| 9,326,792 B2 | 5/2016 | Dickinson et al. |
| 9,364,280 B2 | 6/2016 | Zarins et al. |
| 9,402,560 B2 | 8/2016 | Organ et al. |
| 9,414,885 B2 | 8/2016 | Willard |
| 9,439,728 B2 | 9/2016 | Hull et al. |
| 9,445,868 B2 | 9/2016 | Hull et al. |
| 9,452,015 B2 | 9/2016 | Kellerman et al. |
| 9,486,276 B2 * | 11/2016 | Rios .................. A61B 18/1492 |
| 9,510,901 B2 | 12/2016 | Steinke et al. |
| 9,623,217 B2 | 4/2017 | Pillai |
| 9,706,998 B2 | 7/2017 | Dickinson et al. |
| 9,782,201 B2 | 10/2017 | Dickinson et al. |
| 9,782,533 B2 | 10/2017 | Brenneman et al. |
| 10,045,817 B2 | 8/2018 | Miller et al. |
| 10,265,206 B2 | 4/2019 | Heuser et al. |
| 10,517,637 B2 | 12/2019 | Dickinson et al. |
| 10,543,308 B2 | 1/2020 | Lenihan et al. |
| 10,575,974 B2 | 3/2020 | De Pablo Pena et al. |
| 10,596,356 B2 | 3/2020 | Lenihan et al. |
| 2001/0029384 A1 | 10/2001 | Nicholas et al. |
| 2002/0072739 A1 | 6/2002 | Lee et al. |
| 2002/0113678 A1 | 8/2002 | Creighton |
| 2002/0151945 A1 | 10/2002 | Gobin et al. |
| 2003/0009163 A1 | 1/2003 | Messing et al. |
| 2003/0220674 A1 | 11/2003 | Anderson et al. |
| 2004/0059211 A1 | 3/2004 | Patel et al. |
| 2004/0059280 A1 | 3/2004 | Makower et al. |
| 2004/0167506 A1 | 8/2004 | Chen |
| 2004/0215220 A1 * | 10/2004 | Dolan .................. A61B 17/11 606/153 |
| 2004/0236360 A1 | 11/2004 | Cohn et al. |
| 2005/0033401 A1 | 2/2005 | Cunniffe et al. |
| 2005/0065509 A1 | 3/2005 | Coldwell et al. |
| 2005/0245925 A1 | 11/2005 | Iki et al. |
| 2005/0251120 A1 | 11/2005 | Anderson et al. |
| 2006/0079897 A1 | 4/2006 | Harrison et al. |
| 2006/0111704 A1 | 5/2006 | Brenneman et al. |
| 2007/0173878 A1 | 7/2007 | Heuser |
| 2007/0185567 A1 | 8/2007 | Heuser et al. |
| 2007/0203515 A1 | 8/2007 | Heuser et al. |
| 2007/0203572 A1 | 8/2007 | Heuser et al. |
| 2008/0021532 A1 | 1/2008 | Kveen et al. |
| 2008/0051626 A1 | 2/2008 | Sato et al. |
| 2008/0065019 A1 | 3/2008 | Heuser et al. |
| 2008/0091192 A1 | 4/2008 | Paul et al. |
| 2008/0119879 A1 | 5/2008 | Brenneman et al. |
| 2008/0140061 A1 | 6/2008 | Toubia et al. |
| 2008/0161901 A1 | 7/2008 | Heuser et al. |
| 2008/0171944 A1 | 7/2008 | Brenneman et al. |
| 2008/0183164 A1 | 7/2008 | Elkins et al. |
| 2008/0188848 A1 | 8/2008 | Deutmeyer et al. |
| 2008/0221519 A1 | 9/2008 | Schwach et al. |
| 2008/0275442 A1 | 11/2008 | Paul et al. |
| 2008/0312577 A1 | 12/2008 | Drasler et al. |
| 2009/0036872 A1 | 2/2009 | Fitzgerald et al. |
| 2009/0076324 A1 | 3/2009 | Takayama et al. |
| 2009/0112119 A1 | 4/2009 | Kim |
| 2009/0118722 A1 | 5/2009 | Ebbers et al. |
| 2009/0124847 A1 | 5/2009 | Doty et al. |
| 2009/0187098 A1 | 7/2009 | Makower et al. |
| 2009/0198232 A1 | 8/2009 | Young et al. |
| 2009/0248148 A1 | 10/2009 | Shaolian et al. |
| 2009/0275876 A1 | 11/2009 | Brenneman et al. |
| 2009/0281379 A1 | 11/2009 | Binmoeller et al. |
| 2009/0318849 A1 | 12/2009 | Hobbs et al. |
| 2010/0004623 A1 | 1/2010 | Hamilton, Jr. et al. |
| 2010/0010488 A1 | 1/2010 | Kassab et al. |
| 2010/0082058 A1 * | 4/2010 | Kassab .................. A61F 2/06 606/194 |
| 2010/0130835 A1 | 5/2010 | Brenneman et al. |
| 2010/0198206 A1 | 8/2010 | Levin |
| 2010/0204691 A1 | 8/2010 | Bencini |
| 2010/0222664 A1 | 9/2010 | Lemon et al. |
| 2010/0256616 A1 | 10/2010 | Katoh et al. |
| 2010/0280316 A1 | 11/2010 | Dietz et al. |
| 2010/0280514 A1 | 11/2010 | Zerfas |
| 2010/0286705 A1 | 11/2010 | Vassiliades, Jr. |
| 2010/0292685 A1 | 11/2010 | Katoh et al. |
| 2010/0298645 A1 | 11/2010 | Deutch |
| 2011/0015657 A1 | 1/2011 | Brenneman et al. |
| 2011/0112427 A1 | 5/2011 | Phillips et al. |
| 2011/0118735 A1 | 5/2011 | Abou-Marie et al. |
| 2011/0201990 A1 | 8/2011 | Franano |
| 2011/0213309 A1 | 9/2011 | Young et al. |
| 2011/0218476 A1 | 9/2011 | Kraemer et al. |
| 2011/0270149 A1 | 11/2011 | Faul et al. |
| 2011/0288392 A1 | 11/2011 | de la Rama et al. |
| 2011/0288544 A1 | 11/2011 | Verin et al. |
| 2011/0306959 A1 | 12/2011 | Kellerman et al. |
| 2011/0306993 A1 | 12/2011 | Hull et al. |
| 2011/0319976 A1 | 12/2011 | Iyer et al. |
| 2012/0010556 A1 | 1/2012 | Faul et al. |
| 2012/0022518 A1 | 1/2012 | Levinson |
| 2012/0035539 A1 | 2/2012 | Tegg |
| 2012/0046678 A1 * | 2/2012 | LeMaitre ....... A61B 17/320725 606/159 |
| 2012/0059398 A1 | 3/2012 | Pate et al. |
| 2012/0065652 A1 | 3/2012 | Cully et al. |
| 2012/0078342 A1 | 3/2012 | Vollkron et al. |
| 2012/0089123 A1 | 4/2012 | Organ et al. |
| 2012/0101423 A1 | 4/2012 | Brenneman |
| 2012/0116354 A1 | 5/2012 | Heuser |
| 2012/0157992 A1 | 6/2012 | Smith et al. |
| 2012/0209377 A1 | 8/2012 | Machold et al. |
| 2012/0215088 A1 | 8/2012 | Wang et al. |
| 2012/0239021 A1 | 9/2012 | Doty et al. |
| 2012/0277736 A1 | 11/2012 | Francischelli |
| 2012/0281330 A1 | 11/2012 | Abbott et al. |
| 2012/0289953 A1 | 11/2012 | Berzak et al. |
| 2012/0296262 A1 | 11/2012 | Ogata et al. |
| 2012/0302935 A1 | 11/2012 | Miller et al. |
| 2013/0041306 A1 | 2/2013 | Faul et al. |
| 2013/0056876 A1 | 3/2013 | Harvey et al. |
| 2013/0110105 A1 | 5/2013 | Vankov |
| 2013/0172881 A1 | 7/2013 | Hill et al. |
| 2013/0190744 A1 | 7/2013 | Avram et al. |
| 2013/0190754 A1 | 7/2013 | Paul et al. |
| 2013/0216351 A1 | 8/2013 | Griffin |
| 2013/0226170 A1 | 8/2013 | Seddon et al. |
| 2013/0261368 A1 | 10/2013 | Schwartz |

(56) References Cited

U.S. PATENT DOCUMENTS

| | | |
|---|---|---|
| 2013/0282000 A1 | 10/2013 | Parsonage |
| 2013/0296704 A1 | 11/2013 | Magnin et al. |
| 2014/0012251 A1 | 1/2014 | Himmelstein et al. |
| 2014/0031674 A1 | 1/2014 | Newman et al. |
| 2014/0094791 A1 | 4/2014 | Hull et al. |
| 2014/0100557 A1 | 4/2014 | Bohner et al. |
| 2014/0100562 A1 | 4/2014 | Sutermeister et al. |
| 2014/0107642 A1* | 4/2014 | Rios .................. A61B 18/1492 606/41 |
| 2014/0166098 A1 | 6/2014 | Kian et al. |
| 2014/0188028 A1 | 7/2014 | Brenneman et al. |
| 2014/0276335 A1* | 9/2014 | Pate .................... A61M 1/3655 604/8 |
| 2015/0005759 A1 | 1/2015 | Welches et al. |
| 2015/0011909 A1 | 1/2015 | Holmin et al. |
| 2015/0018810 A1 | 1/2015 | Baust et al. |
| 2015/0057654 A1 | 2/2015 | Leung et al. |
| 2015/0057687 A1 | 2/2015 | Gittard et al. |
| 2015/0080886 A1 | 3/2015 | Miller et al. |
| 2015/0094645 A1 | 4/2015 | Omar-Pasha |
| 2015/0112195 A1 | 4/2015 | Berger et al. |
| 2015/0134055 A1 | 5/2015 | Spence et al. |
| 2015/0141836 A1 | 5/2015 | Naumann et al. |
| 2015/0164573 A1 | 6/2015 | Delaney |
| 2015/0196309 A1 | 7/2015 | Matsubara et al. |
| 2015/0196356 A1 | 7/2015 | Kauphusman et al. |
| 2015/0196360 A1 | 7/2015 | Grantham et al. |
| 2015/0201962 A1 | 7/2015 | Kellerman et al. |
| 2015/0258308 A1 | 9/2015 | Pate |
| 2015/0297259 A1 | 10/2015 | Matsubara et al. |
| 2015/0313668 A1 | 11/2015 | Miller et al. |
| 2015/0320472 A1 | 11/2015 | Ghaffari et al. |
| 2016/0022345 A1 | 1/2016 | Baust et al. |
| 2016/0051323 A1 | 2/2016 | Stigall et al. |
| 2016/0058452 A1 | 3/2016 | Brenneman et al. |
| 2016/0058956 A1 | 3/2016 | Cohn et al. |
| 2016/0067449 A1 | 3/2016 | Misener et al. |
| 2016/0082234 A1 | 3/2016 | Schwartz et al. |
| 2016/0100840 A1 | 4/2016 | Brenneman et al. |
| 2016/0128855 A1 | 5/2016 | Heuser et al. |
| 2016/0135881 A1 | 5/2016 | Katoh et al. |
| 2016/0184011 A1 | 6/2016 | Krishnan |
| 2016/0206317 A1 | 7/2016 | Dickinson et al. |
| 2017/0071627 A1 | 3/2017 | Kellerman et al. |
| 2017/0119464 A1 | 5/2017 | Rios et al. |
| 2017/0172679 A1 | 6/2017 | Doty et al. |
| 2017/0202603 A1 | 7/2017 | Cohn et al. |
| 2017/0202616 A1 | 7/2017 | Pate et al. |
| 2017/0232272 A1 | 8/2017 | Perkins et al. |
| 2017/0252006 A1 | 9/2017 | Tsuruno |
| 2018/0000512 A1 | 1/2018 | Dickinson et al. |
| 2018/0083228 A1 | 3/2018 | Yang et al. |
| 2018/0116522 A1 | 5/2018 | Brenneman et al. |
| 2018/0206845 A1 | 7/2018 | Brenneman et al. |
| 2018/0344396 A1 | 12/2018 | Miller et al. |
| 2020/0038103 A1 | 2/2020 | Pappone et al. |
| 2020/0061338 A1 | 2/2020 | Pate |
| 2020/0178970 A1 | 6/2020 | Berman et al. |

FOREIGN PATENT DOCUMENTS

| | | |
|---|---|---|
| CN | 101730557 A | 6/2010 |
| EP | 0923912 A2 | 6/1999 |
| RU | 2168951 C1 | 6/2001 |
| WO | 9729682 A1 | 8/1997 |
| WO | 9956640 A1 | 11/1999 |
| WO | 2008010039 A2 | 1/2008 |
| WO | 2009005644 A2 | 1/2009 |
| WO | 2011100625 A2 | 8/2011 |
| WO | 2012015722 A1 | 2/2012 |
| WO | 2013112584 A1 | 8/2013 |
| WO | 2014028306 A1 | 2/2014 |
| WO | 2014052919 A1 | 4/2014 |
| WO | 2014153229 A1 | 9/2014 |
| WO | 2015061614 A1 | 4/2015 |
| WO | 2015085119 A1 | 6/2015 |
| WO | 2015108984 A1 | 7/2015 |
| WO | 2016033380 A1 | 3/2016 |
| WO | 2016081321 A2 | 5/2016 |
| WO | 2017124059 A1 | 7/2017 |
| WO | 2017124060 A1 | 7/2017 |
| WO | 2018057095 A1 | 3/2018 |

OTHER PUBLICATIONS

Maybury et al., "The Effect of Roll Angle on the Performance of Halbach Arrays," University of California—San Diego, Center for Magnetic Recording Research (2008), 19 pgs.

Choi, et al., Design of a Halbach Magnet Array Based on Optimization Techniques; IEEE Transactions on Magnetics, vol. 44, No. 10, Oct. 2008, pp. 2361-2366. (Year: 2008).

"Banasik et al. (2011). "A rare variant route of the ulnar artery does not contraindicate the creation of a fistula in the wrist of a diabetic patient with end-stage renal disease," Postepy Hig Med Dosw. 65:654-657."

Bharat et al. (2012). "A novel technique of vascular anastomosis to prevent juxta-anastomotic stenosis following arteriovenous fistula creation," J. Vascular Surgery 55(1):274-280.

Bode et al. (2011 ). "Clinical study protocol for the arch project Computational modeling for improvement of outcome after vascular access creation," J. Vase. Access 12(4):369-376.

Hakim et al., "Ulnar artery-based free forearm flap: Review of Specific anatomic features in 322 cases and related literature," Heand & Neck, Dec. 2013 (published online:2014), Wiley Online Library.

Davidson, I. et al. (2008). "Duplex Ultrasound Evaluation for Dialysis Access Selection and Maintenance: A Practical Guide," The Journal of Vascular Access 9(1 ): 1-9.

Gracz, et al. (1977). "Proximal forearm fistula for maintenance hemodialysis," Kidney International 11 :71-75.

Jennings, WC. et al. (2011). "Primary arteriovenous fistula inflow proximalization for patients at high risk for dialysis access-associated ischemic steal syndrome," J. Vase. Surgery 54(2):554-558.

Kinnaert, et al. (1971). "Ulnar Arteriovenous Fistula for Maintenance Haemodial Ysis," British J. Surgery 58(9):641-643.

Morale et al. (2011). "Venae comitantes as a potential vascular resource to create native arteriovenous fistulae," J. Vase. Access 12(3):211-214.

Shenoy, S. (2009). "Surgical anatomy of upper arm: what is needed for AVF planning," The Journal of Vascular Access 10:223-232.

Vachharajani, T. (2010). "Atlas of Dialysis Vascular Access," Wake Forest University School of Medicine, 77 total pages.

Whittaker et al. (2011). "Prevention better than cure. Avoiding steal syndrome with proximal radial or ulnar arteriovenous fistulae" J. Vase. Access 12(4):318-320.

Extended European Search Report pertaining to EP Patent Application No. 17853586.0, dated Apr. 29, 2020.

International Search Report and Written Opinion pertaining to PCT/US2019/034896, dated May 12, 2020.

\* cited by examiner

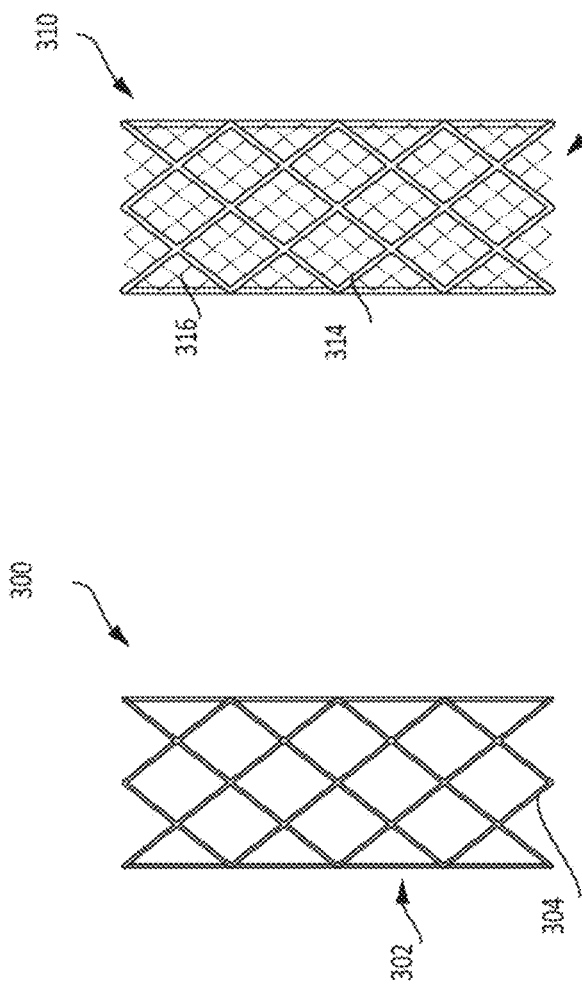
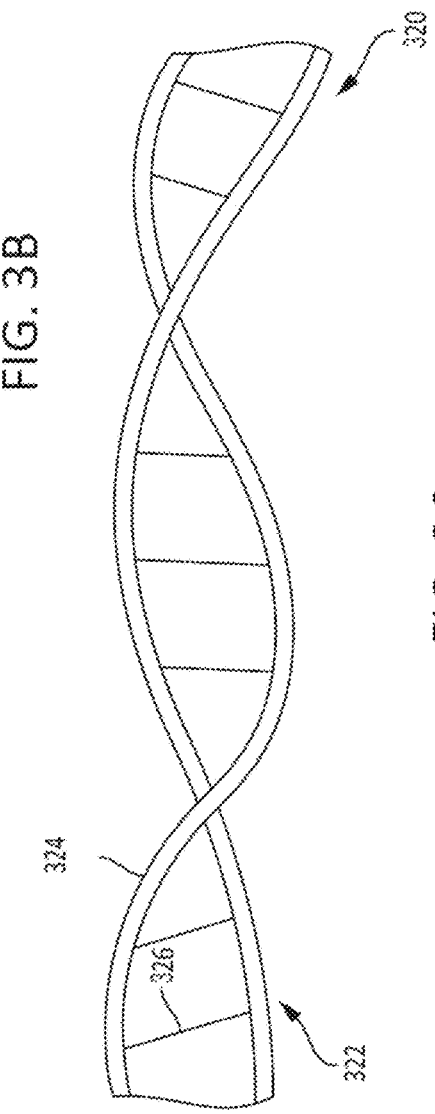
FIG. 3A
FIG. 3B
FIG. 3C

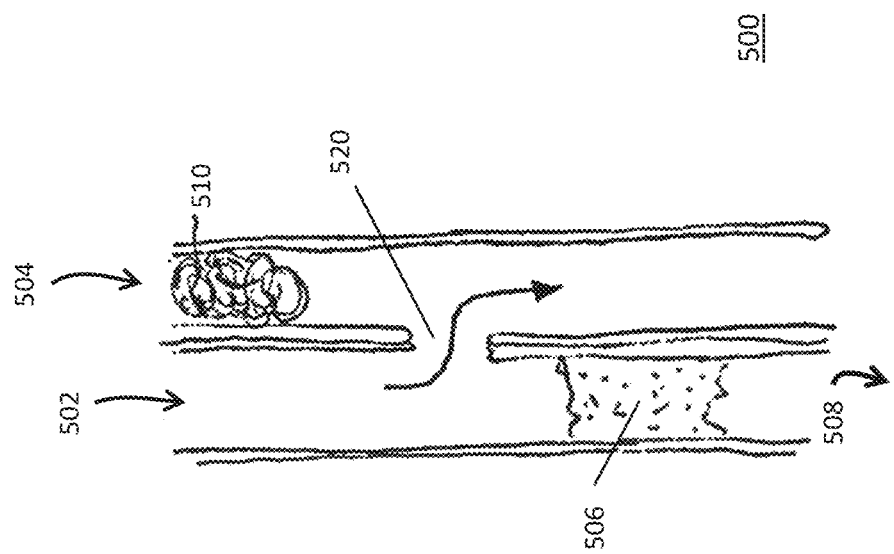

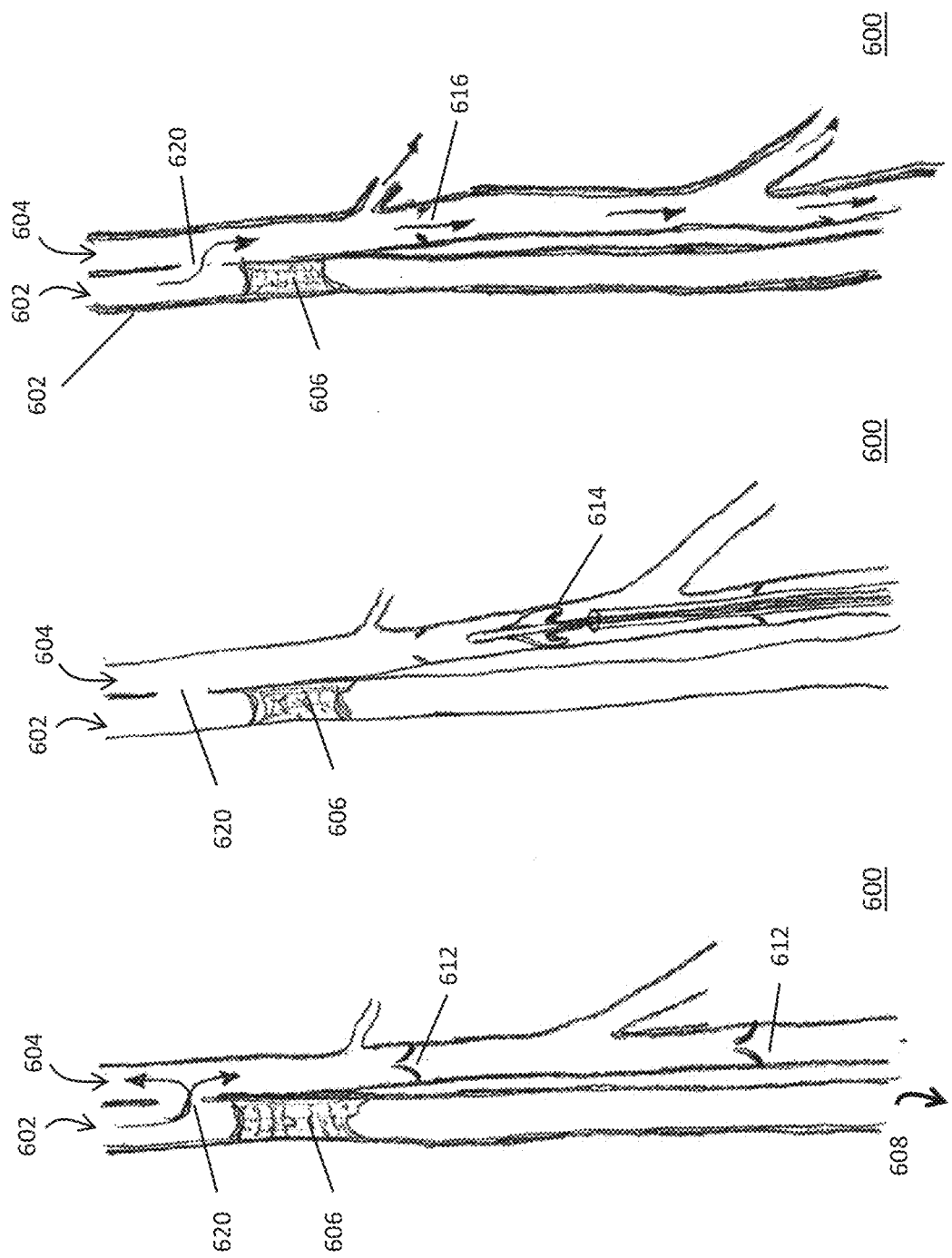

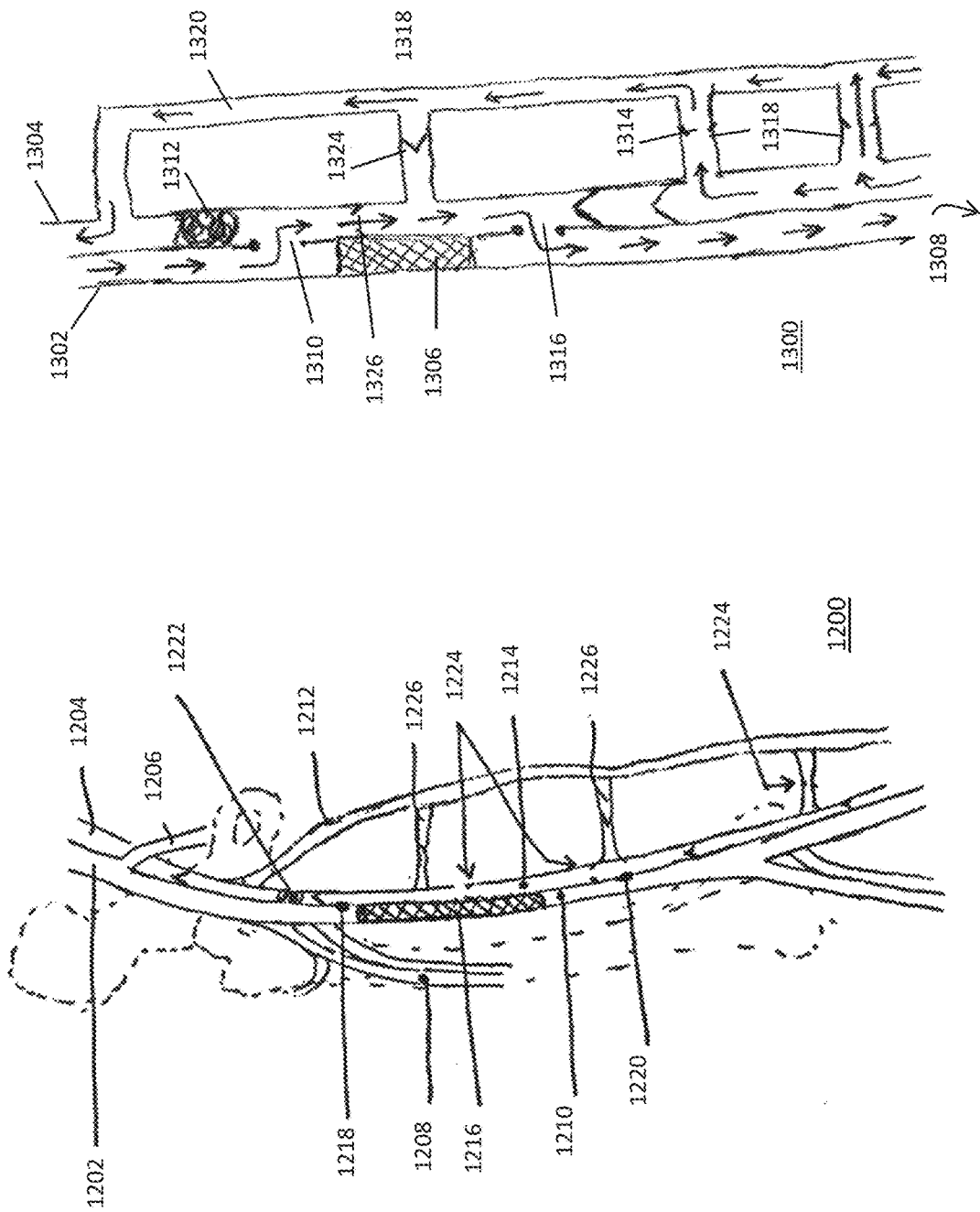

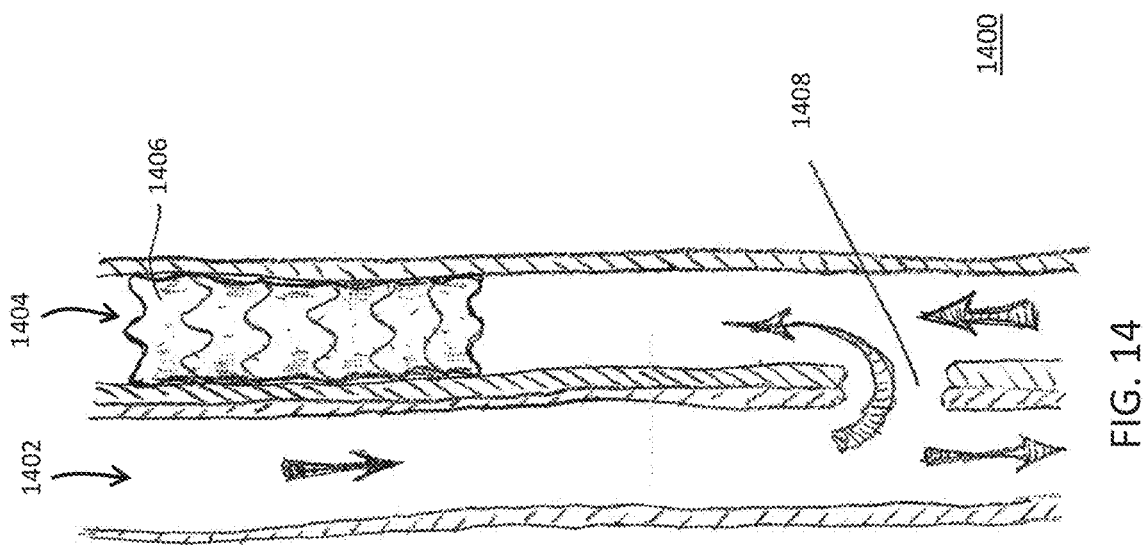

SYSTEMS AND METHODS FOR INCREASING BLOOD FLOW

CROSS-REFERENCE TO RELATED APPLICATIONS

This application claims priority to U.S. Provisional Application No. 62/279,633, filed Jan. 15, 2016, and titled "SYSTEMS AND METHODS FOR INCREASING BLOOD FLOW," U.S. Provisional Application No. 62/399,473, filed Sep. 25, 2016, and titled "SYSTEMS AND METHODS FOR INCREASING BLOOD FLOW," and U.S. Provisional Application No. 62/399,465, filed Sep. 25, 2016, and titled "VASCULAR STENT DEVICES AND METHODS," each of which is hereby incorporated by reference in its entirety.

FIELD

The current invention relates to systems and methods for improving fluid flow in a vessel.

BACKGROUND

It may be desirable in some instances to form a path between a first vessel (e.g., a vein or artery) to a second, nearby vessel (e.g., a second vein or artery), such as a fistula. Forming a fistula between two blood vessels can have one or more beneficial functions. For example, the formation of a fistula between an artery and a vein may provide access to the vasculature for hemodialysis patients. As another example, it may be desirable to form a path between two blood vessels to bypass an occlusion or barrier within one of the vessels to treat of a variety of diseases. Patients may suffer from occluded vessels for a number for reasons, including peripheral vascular disease (PVD), which may progress into critical limb ischemia (CLI) if left untreated. CLI is characterized by chronic pain, as well as tissue loss that may ultimately result in amputation.

It would therefore be useful to find improved ways to access and create alternate paths for blood flow around an occlusion to target ischemic tissues in the peripheral vasculature, as well as for increasing blood flow in the peripheral vasculature for other reasons, such as to increase flow through a venous stent graft.

BRIEF SUMMARY

Described here are devices, systems, and methods for delivering blood flow around an occlusion to ischemic tissues located in the peripheral vasculature. The devices, systems, and methods described herein may be used to form a bypass through a fistula between two blood vessels to bypass an occlusion in a vessel. In some variations, one or more fistulas may be formed to provide one or more of perfusion of ischemic tissue, arterialization of a vein, bypass of an arterial occlusion, and/or improved flow through a venous stent graft. In some variations, the methods described herein comprise methods for improving blood flow in a vessel, comprising advancing a first catheter into a first vessel proximal to an occlusion in the first vessel, wherein the first catheter comprises a fistula-forming element, advancing a second catheter into a second vessel, wherein the second vessel is adjacent to the first vessel, and forming a fistula between the first vessel and the second vessel using the fistula-forming element. The fistula may allow blood to flow past the occlusion through the second vessel. For example, the first vessel may be the femoral artery, and the second vessel may be the femoral vein. In some variations, the fistula-forming element may comprise an electrode, and each of the first and second catheters may comprise a magnet. The method may further comprise providing an embolization coil in the second vessel, and the embolization coil may be located proximal to the occlusion. The method may also further comprise performing a valvulotomy in the second vessel, and the valvulotomy may be performed distal to the fistula. In some variations, the first vessel may be an artery, and the second vessel may be a vein. The method may further comprise advancing a third catheter comprising a second fistula-forming element into the first vessel distal to the occlusion in the first vessel, advancing a fourth catheter into the second vessel, and forming a second fistula between the first vessel and the second vessel using the second fistula-forming element. In some of these variations, the second fistula-forming element may comprise an electrode. In some variations of the methods, the second vessel may contain a stent graft.

In some other variations of the methods, a stent may be deployed over one or more valves in the second vessel. The stent may hold the one or more valves in an open configuration. In some variations, the stent may be deployed proximal to the occlusion. In some of these instances, the stent is deployed proximal to the fistula. The stent may be deployed over the fistula. In some variations, a thrombosis may be formed at a proximal portion of the stent. The thrombosis may be formed at a predetermined rate. In some variations, a stent may be deployed in the second vessel. The stent may extend over both the first and second fistulas.

BRIEF DESCRIPTION OF THE DRAWINGS

FIGS. 3A-3C depict variations of stents described here.

FIG. 5 depicts another variation of a method for perfusing ischemic tissue.

FIGS. 6A-6C depict another variation of a method for perfusing ischemic tissue.

FIG. 12 depicts a variation of a method for bypassing an occlusion in a femoral artery.

FIG. 13 depicts a schematic of the fluid flow of FIG. 12.

FIG. 14 depicts a variation of a method for increasing flow through a venous stent graft.

DETAILED DESCRIPTION

Figure 1B:
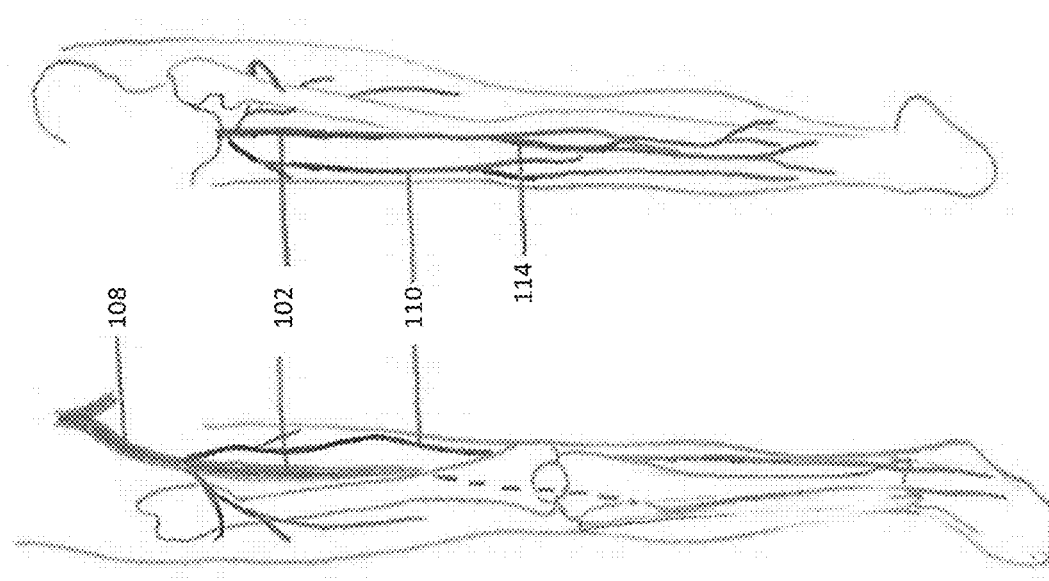
FIGS. 1A-1B are illustrative depictions of a portion of the vascular anatomy of a leg of a human.
Figure 1A:
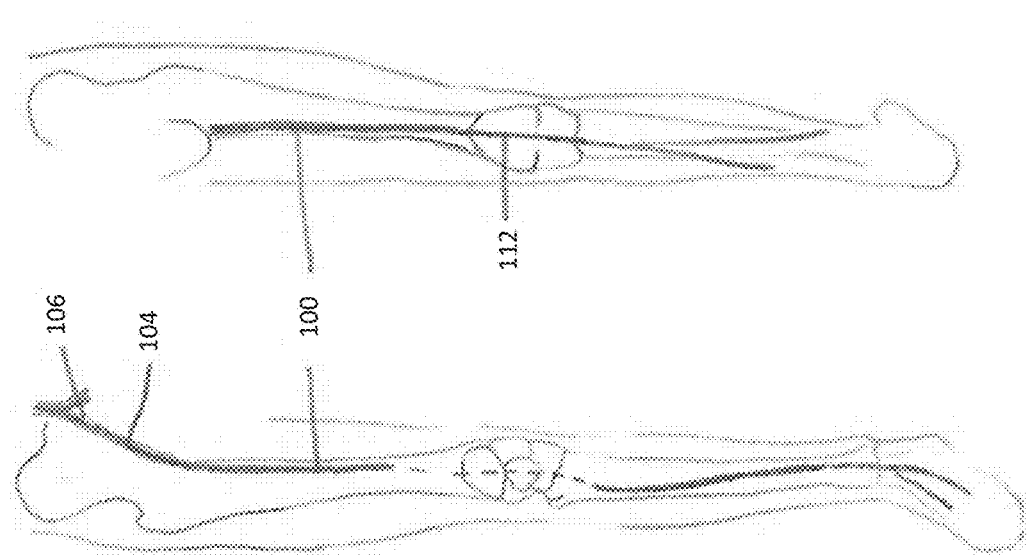

Generally described here are devices, systems, and methods for percutaneously creating one or more arterio-venous fistulae in order to bypass an occlusion or other barrier and to deliver blood flow around an occlusion to ischemic tissues located in the peripheral vasculature, as well as for increasing venous flow, such as for increasing flow through a venous stent graft. FIGS. 1A-1B show a simplified depiction of the typical vascular anatomy of the leg. Specifically, as shown in FIG. 1A, the femoral artery (100) is the main arterial supply to the lower extremities and extends down the thigh. The femoral artery (100) receives blood flow from the external iliac artery (104) and common iliac artery (106) and connects distally to a popliteal artery (112). As shown in FIG. 1B, the femoral vein (102) is the counterpart to the femoral artery (100) and is a continuation of the popliteal vein (114). The saphenous vein (110) is a large, subcutaneous, superficial vein of the leg. The common iliac vein (108) receives venous blood from the femoral vein (102). The iliac artery and vein (106, 108) are located in the pelvis.

Generally, the devices and methods described herein may be used to form a fistula between two blood vessels (e.g., an arteriovenous fistula between an artery and a vein) to shunt blood around one or more vascular occlusions and/or to alter blood flow through the vasculature, which may thereby increase blood flow to ischemic tissues. In some variations, the systems and methods may be used to form a fistula proximal to an occlusion and/or distal to an occlusion, to bypass an occlusion in an artery or vein and establish fluid flow around the occlusion. Generally, to form a path around an occlusion or barrier using one or more fistulas between two blood vessels, one or more catheters may be advanced in a minimally invasive fashion through the vasculature to a target location (e.g., at or near the occlusion or barrier). In some instances, a single catheter may be placed in a blood vessel to form a fistula with an adjoining blood vessel. In other instances, a system comprising multiple catheters may be used to form one or more fistulas. For example, in some instances a catheter may be placed in each of the two blood vessels. For instance, a first catheter may be advanced within the occluded vessel to a proximal and/or distal side of the occlusion or barrier, and a second catheter may be advanced through an adjacent (or otherwise nearby) vessel or cavity. In these instances, it should be appreciated that each catheter may or may not have the same configuration of elements, and that some catheters may be different from and/or complementary to other catheters.

Generally, the systems described herein comprise one or more catheters. The one or more catheters generally comprise a fistula-forming element. The fistula-forming element may be an electrode that is used to form the fistula such as through tissue ablation. The catheter may further comprise one or more alignment features, such as magnets, flat coaption surfaces, visual alignment aids, and/or handles that help align one catheter relative to another catheter in related blood vessels and/or bring the catheters (and blood vessels) in closer approximation. These devices and systems offer a minimally invasive approach, having improved procedural speed and a reduced likelihood of bypass thrombosis due to the elimination of foreign materials such as grafts and stents in some variations.

Generally, the systems and methods described here may be used to increase retrograde flow of blood through a vessel (e.g., a vein segment concomitant to an arterial occlusion). The peripheral vasculature generally comprises uni-directional venous valves that aid the return of venous blood back to the heart. In some variations, a valvulotome may be used to perform a valvulotomy by cutting the leaflets of one or more unidirectional venous valves. By rendering the venous valves incompetent, blood flow through a fistula system may have a retrograde path through the vein. In other variations, the systems and methods may further comprise one or more stents configured to be used in a venous blood vessel to provide the retrograde blood flow path in a concomitant vein segment around the occlusion. Generally, to form a retrograde blood flow path around an occlusion or barrier using one or more stents, a stent may be advanced through the vasculature to a target location in a blood vessel (e.g., in a vein segment opposing the occlusion or barrier in an artery). The stent may be placed in a peripheral vein to hold one or more venous valves open to permit retrograde blood flow through the vein. For example, the sidewalls of the stent may push and hold open one or more unidirectional valves in the vein. Opening the valves using a stent may allow arterialized blood flow from the fistula to flow retrograde through the vein without removing the venous valves.

I. Systems

Figure 2:
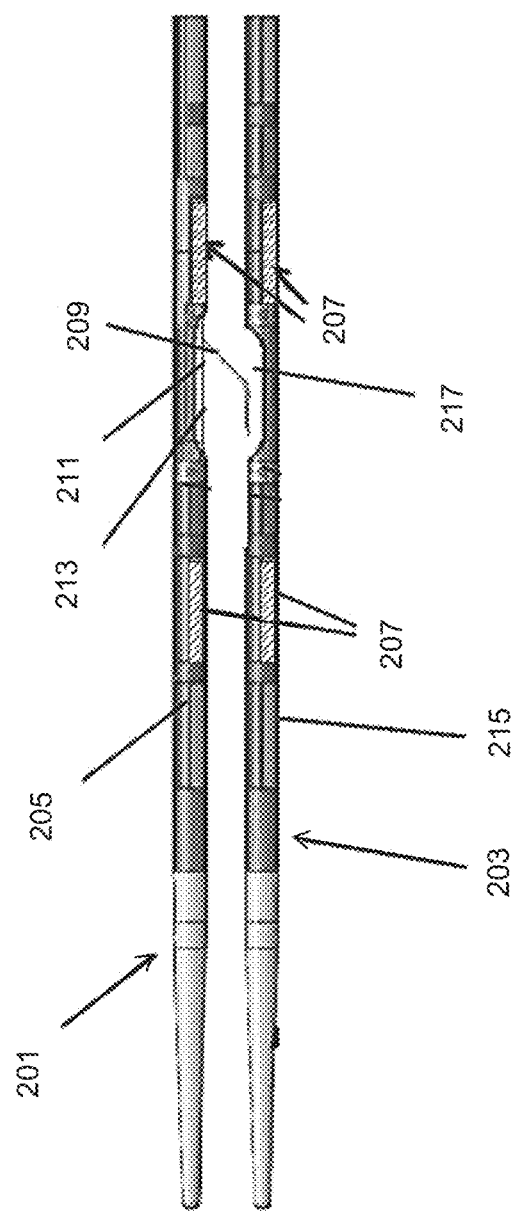
FIG. 2 is an illustrative depiction of a variation of a system described here comprising a first catheter and a second catheter.

Generally, the systems described here comprise one or more catheters configured to be used to form a fistula. FIG. 2 shows an illustrative variation of a catheter system that may be used to form a fistula as described herein. As shown there, the system may comprise a first catheter (201) and a second catheter (203). The first catheter (201) may comprise a catheter body (205), one or more magnetic elements (207), and a fistula-forming element (209) that may be used to form a fistula. In some variations, the fistula-forming element (209) may be advanced to project out of an opening (211) in the catheter body (205). The fistula-forming element (209) may comprise an electrode configured to move between a low-profile configuration and an extended configuration in which it extends from the catheter body (205). In some variations the fistula-forming element may be spring-biased toward the extended configuration. That is, the electrode may be configured to self-expand from the low-profile configuration to the extended configuration. Put yet another way, the electrode (106) may be in its natural resting state in the extended configuration. In some variations of electrodes moving between a low-profile configuration and an extended configuration, the electrode may be held in the low-profile configuration during placement of the catheter. For example, in some variations the electrode may be held in the low-profile configuration by the catheter body. The electrode may be released from the low-profile configuration when the electrode has been delivered to the location for fistula formation. For example, in some variations, the electrode may be released by moving the electrode in a proximal direction relative to the housing using a proximal control, as described in in U.S. patent application Ser. No. 13/298,169, filed on Nov. 16, 2011, and titled "DEVICES AND METHODS FOR FORMING A FISTULA," which is hereby incorporated by reference in its entirety. In other variations, the electrode may be held in a low-profile configuration by an external radially inward force on the electrode from a vessel wall during delivery, as described in U.S. patent application Ser. No. 15/406,755 filed concurrently herewith, titled "DEVICES AND METHODS FOR FORMING A FISTULA" and claiming the benefit of U.S. Provisional Application No. 62/399,471, filed Sep. 25, 2016,and U.S. Provisional Application No. 62/279,603, filed Jan. 15, 2016, which is hereby incorporated by reference in its entirety.

In some variations, the first catheter (201) may comprise a housing (213), which may help protect other components of the first catheter (201) during fistula formation. For example, when the fistula-forming element (209) comprises an electrode configured to ablate tissue, the housing (213) may comprise one or more insulating materials which may shield or otherwise protect one or more components of the first catheter (201) from heat that may be generated by the electrode during use.

As shown in FIG. 2, the second catheter (203) may also comprise a catheter body (215) and one or more magnetic elements (207). In variations where the first catheter (201) comprises a fistula-forming element (209) configured to project out the catheter body (205) of the first catheter (201), such as the variation depicted in FIG. 2, the catheter body (215) of the second catheter (203) may comprise a recess (217) therein, which may be configured to receive the fistula-forming element (209) as it passes through tissue. While shown in FIG. 2 as having a recess (217), it should also be appreciated that in some variations the second catheter (203) may not comprise a recess (217). In some variations, the second catheter may comprise a fistula-forming element (not shown) in addition to or instead of the fistula-forming element (209) of the first catheter (209). Thus, in some variations, a fistula may be formed by one or more electrodes of one catheter, while in other variations, two catheters each comprising an electrode may simultaneously cut tissue from opposing sides to form a fistula.

Certain exemplary devices and systems that may be used in the methods described herein are described in more detail in U.S. patent application Ser. No. 13/298,169, filed on Nov. 16, 2011, and titled "DEVICES AND METHODS FOR FORMING A FISTULA," and are described in more detail in U.S. patent application Ser. No. 15/406,755 filed concurrently herewith, titled "DEVICES AND METHODS FOR FORMING A FISTULA" and claiming the benefit of U.S. Provisional Application No. 62/399,471, filed Sep. 25, 2016, and U.S. Provisional Application No. 62/279,603, filed Jan. 15, 2016, each of which was previously incorporated by reference in its entirety.

The systems described here may further comprise one or more stents to hold open one or more valves of a venous blood vessel. Generally, the stents may comprise a plurality of struts forming a cylindrical configuration. The stent may be placed in a blood vessel to hold the valves in an open configuration that allows bi-directional blood flow, and in particular, retrograde blood flow through a vein for perfusion of ischemic tissue. Accordingly, the stent may be of minimal thickness and surface area (e.g., diaphanous) to limit platelet activation and stenosis. In some variations, a stent may hold one or more valves open, allow blood flow from a fistula to pass through a sidewall of the stent, provide structural support to the fistula, and/or be configured to form a thrombus at a proximal portion of the stent to drive arterial blood flow distally through the vein.

In some variations, the stent may have an outer diameter between about 1 mm and about 20 mm. In some variations, the stent may have a strut width and thickness between about 0.05 mm and about 0.5 mm. In some variations, the stent may have side aperture openings between about 1 mm and about 15 mm in length and between about 1 mm and about 15 mm in width. For example, the stent may have an outer diameter of about 5.0 mm, a strut width of about 0.05 mm, a strut thickness of about 0.05 mm, and one or more diamond shaped apertures of about 5 mm in width and about 10 mm in length.

In some variations an axial portion of the stent may comprise a plurality of struts. For example, an axial portion of the stent may comprise a minimum of four struts to provide a minimum desired strut-to-leaflet ratio to achieve adequate valve leaflet opening. In some instances the strut width and a mesh density of the stent may be minimized so as to achieve a minimum stent area-to-intimal area ratio. The stent may comprise any suitable configuration, such as a tube configuration and/or helical spiral configuration.

The stent may be deployed by self-expansion or balloon expansion. For instance, a self-expanding stent in a compressed configuration may be constrained by a stent delivery system (e.g., a system comprising a conduit configured to hold the self-expanding stent in a compressed configuration) as it is advanced through vasculature in a minimally invasive manner. Upon release from the stent delivery system, the self-expanding stent may transition to an expanded configuration. Similarly, a balloon-expandable stent in a compressed configuration may be coupled to a stent delivery system comprising a balloon as it is advanced through vasculature in a minimally invasive manner. At a deployment location, the balloon of the stent delivery system may be inflated to expandably deform the stent to an expanded configuration. After the balloon is deflated, the stent may remain in the expanded configuration within the target vessel.

In some variations, the stent may have multiple portions, each portion corresponding to a specific material, shape, and/or coating. For example, the stent may comprise a proximal portion comprising a coating for inducing thrombosis and a distal portion configured to prevent platelet aggregation and maximize fluid flow through the vessel. Of course, the stent may comprise any suitable number of portions, e.g., two, three, or four portions, and the length of each portion may be the same as or different from the other portions. The stent may comprise any suitable length, and the length of the stent may vary depending on the type of procedure being performed. In some variations, the stent may have a length between about 5.0 cm and about 60 cm. For example, the stent may have a length of about 15 cm. The stent may be configured to fit within a lumen of a target blood vessel and press against the leaflets of a valve, such that they are moved into and held in an open configuration.

The stent may be made of any suitable material, for example, one or more metals or polymers (e.g., stainless steel 316L, tantalum, nitinol, platinum iridium, niobium alloy, cobalt alloy, etc.). The stent may optionally be bioresorbable (e.g., made of poly-L lactic acid (PLLA) and may absorb over a time period of six months to three years) and may optionally comprise a drug eluting coating. The stent may be formed by any suitable manufacturing process, for example, laser cutting, photochemical etching, braiding, knitting, vapor deposition, water jet, etc. In some variations, the stent may comprise one or more coverings and/or visualization markers to aid in locating and positioning the stent within a vessel. For example, the stent may comprise a radiopaque marker and/or coating made of one or more of gold, platinum, tantalum, etc. that may be indirectly visualized.

FIGS. 3A-3C show illustrative variations of stent geometries that may be used to increase retrograde blood flow in venous vasculature. FIG. 3A shows a portion of a stent (300). As shown there, the stent (300) may comprise a plurality of struts (304) forming a repeating symmetric diamond pattern, which form a tubular configuration (302). It should be understood that many different configurations of the stent pattern may be used to provide a structure capable of holding the valve leaflets open. Patterns may include a helical coil or coils, rings of straight, angled, zig-zag, or curved geometries interconnected by linking elements, or braided or woven meshes. Another variation is illustrated in FIG. 3B, which shows a portion of a stent (310) comprising a plurality of first struts (314) and a plurality of second struts (316) forming a tubular configuration (312). The first struts (314) may be thicker (e.g., have a larger diameter) than the second struts (316). In one example, the first struts (314) may form a first set of diamonds, and the second struts (316) may form a second set of smaller diamonds within the larger diamonds. As shown, nine smaller diamonds form a larger diamond. In some variations, the second struts (316) may be disposed on the interior side of the first struts (314). The first struts (314) may be configured to provide radial strength to a blood vessel in which the stent (310) is disposed. The second struts (316) may be configured to hold open the valves. In yet another variation, as shown in FIG. 3C, a stent (320) may comprise a helical configuration. For example, the stent (320) may comprise a double helix (322) comprising two helical elongate struts (324) and a plurality of connecting struts (326).

II. Methods

Described herein are methods for forming a fistula between two blood vessels. The two blood vessels may be two closely-associated blood vessels, such as a vein and an artery, two veins, two arteries, or the like. Generally, the methods described here comprise accessing a first blood vessel with a first catheter, and advancing the first catheter to a target location within a first blood vessel. A second blood vessel may be accessed with a second catheter, and the second catheter may be advanced to a target location within the second vessel. After the vessels are brought toward each other and the catheters are aligned (e.g., axially and rotationally aligned), one or more fistula-forming elements may be activated to bore through, perforate, or otherwise create a passageway between the two blood vessels such that blood may flow directly between the two adjoining blood vessels. When such a fistula is formed, hemostasis may be created without the need for a separate device or structure (e.g., a suture, stent, shunt, or the like) connecting or joining the blood vessels.

Advancement of one or more catheters through a vessel to a target site is not particularly limited. In some variations, a first catheter is advanced into an artery, and a second catheter is advanced into a vein. In other variations, a first catheter is advanced into a first vein, and a second catheter is advanced into a second vein. In still other variations, a first catheter is advanced into a first artery and a second catheter is advanced into a second artery. In some variations, a first catheter is advanced into a vein, and the second catheter is advanced into an artery. The first and/or second catheters may be advanced over a guidewire or in any suitable manner and advancement may or may not occur under indirect visualization (e.g., via fluoroscopy, X-ray, or ultrasound).

In some variations, the methods described herein may comprise aligning the first and second catheters. This may comprise axially and/or rotationally aligning the catheters. For example, the catheters may be oriented such that a fistula-forming element of at least one of the first or second catheters is positioned to form a fistula in a certain location. In variations where both the first and second catheters comprise fistula-forming elements (e.g., an active electrode and a ground electrode, or each an active electrode), the catheters may be oriented to align these fistula-forming elements relative to each other. The catheters may be aligned in any suitable manner. The first and second catheters may comprise any suitable combination of one or more alignment features. In some variations, each of the first and second catheters may comprise one or more magnets, which may generate an attractive force between the first and second catheters. This may pull the catheters toward each other and/or help to rotationally align them. Once the catheter or catheters are in position, one or more fistula-forming elements may be used to create a fistula between the two blood vessels, as described in more detail in U.S. patent application Ser. No. 13/298,169, filed on Nov. 16, 2011, and titled "DEVICES AND METHODS FOR FORMING A FISTULA," and as described in more detail in U.S. patent application Ser. No. 15/406,755 filed concurrently herewith, titled "DEVICES AND METHODS FOR FORMING A FISTULA" and claiming the benefit of U.S. Provisional Application No. 62/399,471,filed Sep. 25, 2016, and U.S. Provisional Application No. 62/279,603, filed Jan. 15, 2016, each of which was previously incorporated by reference in its entirety.

A. Arterial Occlusion

Generally, the methods described here comprise forming a fistula to perfuse ischemic tissue. In some variations, the fistula may improve perfusion of tissue distal to fistula creation. In yet other variations, the methods may form an arterial occlusion bypass by arterializing a vein segment. In one variation, an in situ-femoral-popliteal occlusion bypass may be provided by creating a percutaneous arteriovenous fistula that arterializes a concomitant vein segment around a femoral artery occlusion.

Figure 4C:
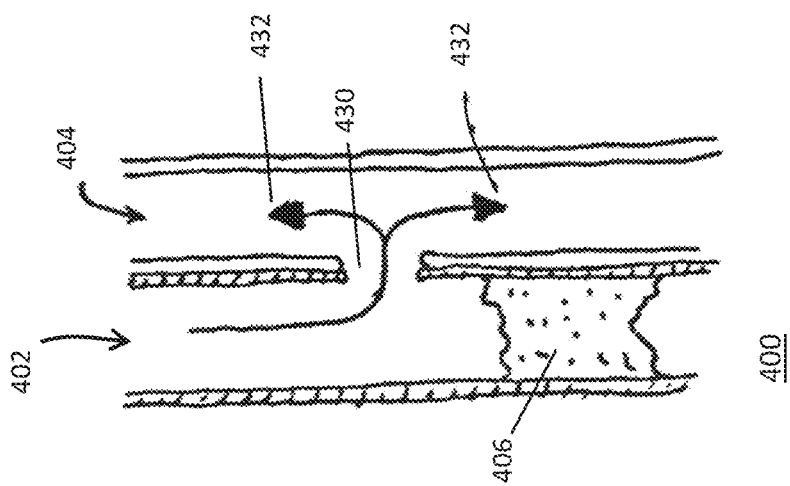
FIGS. 4A-4C depict a variation of a method for perfusing ischemic tissue.
Figure 4B:
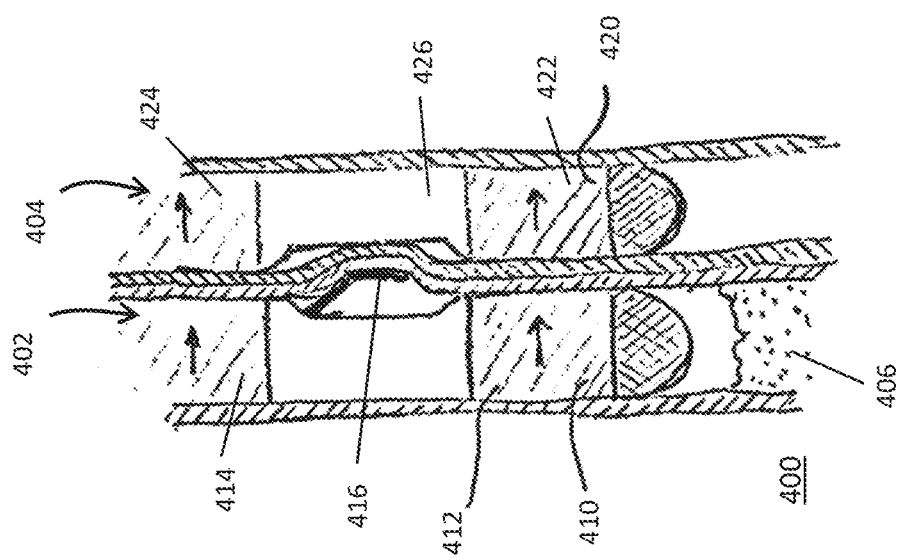
Figure 4A:
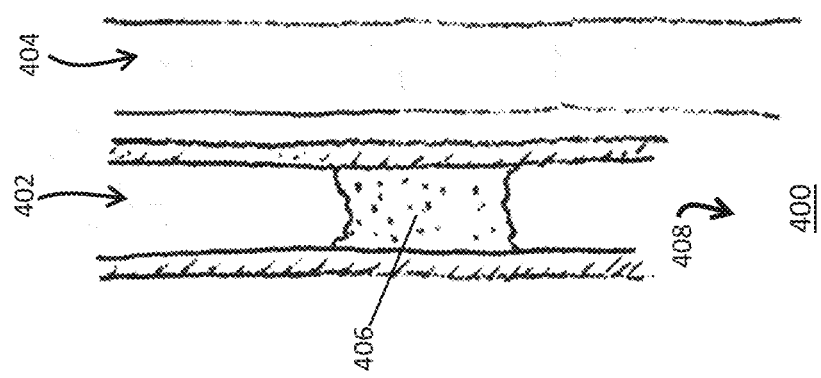

FIG. 4A is a diagram of vasculature (400) including an occlusion (406) such as an atheroma in an artery (402) that forms a distal ischemia (408). The one or more catheters as described above may be advanced into each of the artery (402) and concomitant vein (404). FIG. 4B illustrates the vasculature (400) with a first catheter (410) advanced into the artery (402) proximal to the occlusion (406). The first catheter (410) may be positioned at a fistula formation site for forming a fistula using a fistula-forming element (416) such as an electrode, electrocautery mechanism, mechanical cutting elements, and so forth. The second catheter (420) may be positioned at the fistula formation site within the concomitant vein (404).

In some variations, the first catheter (410) may comprise alignment features including magnets (412, 414) for bringing the first catheter (410) into close approximation with the second catheter (420) in the vein (404). The magnets (412, 414) of the first catheter (410) may coapt with corresponding magnets (422, 424) of the second catheter (420) to compress vessel tissue interposed there between and to align the catheters rotationally and/or axially with each other. The magnets (412, 414, 422, 424) may have polarities as illustrated by arrows in FIG. 4B. In some variations, the vessels may be analyzed and modified prior to fistula formation. Once a fistula-forming element (e.g., electrode) is deployed or otherwise in position to ablate tissue, the fistula-forming element may be used to create a fistula. For example, when the fistula-forming element is an electrode, radiofrequency energy may be applied to the tissue via the electrode to create the fistula. Measurements and/or other procedures may be performed during and/or after ablation to confirm fistula formation. After formation of a fistula and removal of the catheters, blood (432) may flow through the fistula (430) as shown in FIG. 4C. In particular, the fistula (430) and subsequent flow (432) may arterialize the vein (404) and may provide distal retrograde venous flow to treat ischemic tissue. Optionally, a stent may be placed after fistula formation but need not. For example, one or more stents may be deployed in a vein segment concomitant to the fistula (430) to frustrate one or more venous valves (not shown) distal to the fistula and increase retrograde perfusion of ischemic tissue, as discussed in more detail herein. Analysis and modification prior to fistula formation, and measurements and other procedures performed during and/or after ablation, are described in more detail in U.S. patent application Ser. No. 15/406,755 filed concurrently herewith, titled "DEVICES AND METHODS FOR FORMING A FISTULA" and claiming the benefit of U.S. Provisional Application No. 62/399,471, filed Sep. 25, 2016, and U.S. Provisional Application No. 62/279,603, filed Jan. 15, 2016, which was previously incorporated by reference in its entirety.

In some variations, additional steps may be performed to improve perfusion of tissue distal to a fistula and/or bypass an occlusion. FIG. 5 is a diagram of vasculature (500) including an occlusion (506) in an artery (502) that forms a distal ischemia (508). FIG. 5 shows a fistula (520) formed between the artery (502) and vein (504) such as described above with respect to FIGS. 4B-4C. One or more embolization coils (510) may be provided in a vein segment proximal to the fistula (520) to force venous blood flow created by the fistula (520) to flow distally and thereby further increase perfusion of distal ischemic tissue. The coil (510) may help divert arterial flow unidirectionally away from the heart. Alternatively, in some variations, one or more thrombogenic stents may be provided in a vein segment proximal to the occlusion (506). The stent may form a thrombus at a predetermined rate in the vein segment proximal to the fistula (520). Therefore, arterial blood flow through the fistula (520) may be diverted distally to flow retrograde through the vein (504) at a predetermined rate. By forming a thrombus proximal to the fistula (520) at a predetermined rate, the fistula (520) may endothelialize prior to full pressurization of the fistula (520) caused by the proximal thrombus. Additionally or alternatively, an anastomosis or a surgical ligature may be performed in the vein (504) proximal the fistula (520).

Additionally or alternatively, a valvulotomy may be performed in a vein to improve perfusion of tissue distal to a fistula by allowing increased distal flow through the vein. FIG. 6A is a diagram of vasculature (600) including an occlusion (606) in an artery (602) that forms a distal ischemia (608). The vasculature (600) is shown after a fistula (620) has been formed between the artery (602) and vein (604) using the techniques described herein. Once the fistula (620) is formed, the venous valves (612) distal to the fistula (620) may limit retrograde perfusion. These venous valves typically allow unidirectional blood flow. As shown in FIG. 6B, in some variations a valvulotome (614) may be used to perform the valvulotomy. The valvulotome (614) may be advanced through the vein (604) to frustrate one or more of the valves (612) in the vein (604) to increase distal flow through the vein (604) resulting from fistula (620). The valvulotome (614) may be sheathed as it is advanced through vasculature to protect the blood vessel from one or more cutting elements (e.g., blades) of the valvulotome. The valvulotome (614) may be advanced through the vein (604) against venous flow and through the valves (612), then may be brought back with venous flow to perform the valvulotomy. Indirect visualization techniques such as contrast injection may be used to visualize and locate a desired venous valve (612) for the valvulotome to cut. Once the valve (612) is located and the valvulotome (614) is positioned, the valvulotome may be unsheathed and the cutting element may be used to cut the leaflets of the venous valve. The valvulotome (614) may be resheathed, and then the process may be repeated for each venous valve to be cut. FIG. 6C shows venous blood flow after the valvulotomy and removal of the valvulotome from the vein (604). In particular, the frustrated valves (616) increase retrograde perfusion of ischemic tissue. In other variations, a cutting balloon or an excimer laser may be used to render the desired valves incompetent.

In other variations, one or more stents may be used in a vein segment to hold open one or more venous valves, permit retrograde blood flow, and/or form a thrombus in the vein proximal to a fistula. One or more stents may be provided to hold one or more venous valves distal to the fistula to frustrate the valves without cutting them. For instance, contact of the stent with the venous valves provides the force to hold the leaflets of the valves in an open configuration. Furthermore, deployment of the stent may be faster and simpler than use of a valvulotome. For instance, deployment of the stent in a vessel may be performed without valve visualization (e.g., contrast injection) due to the symmetric and repeating configuration of the stent. For instance, following fistulae creation between an artery and vein proximal and distal to the arterial occlusion, a stent may be deployed in the vein by advancing the stent delivery catheter into the vein from a distal access site to a location proximal to the proximal fistula so that the stent delivery catheter may span the region where the stent is to be deployed. A length of the stent may be varied based on a desired length of retrograde blood flow in the vessel. For example, a longer stent disposed in a vein segment will cover and render incompetent a greater number of venous valves and thus improve distal blood flow along a greater length of the vein. It should be appreciated that a stent may extend distally and/or proximally beyond one or more fistulas such that the stent may overlap the one or more fistulas. In these cases, blood flow from an artery through the fistula may pass through a sidewall of the stent and into a vein.

Figure 7:
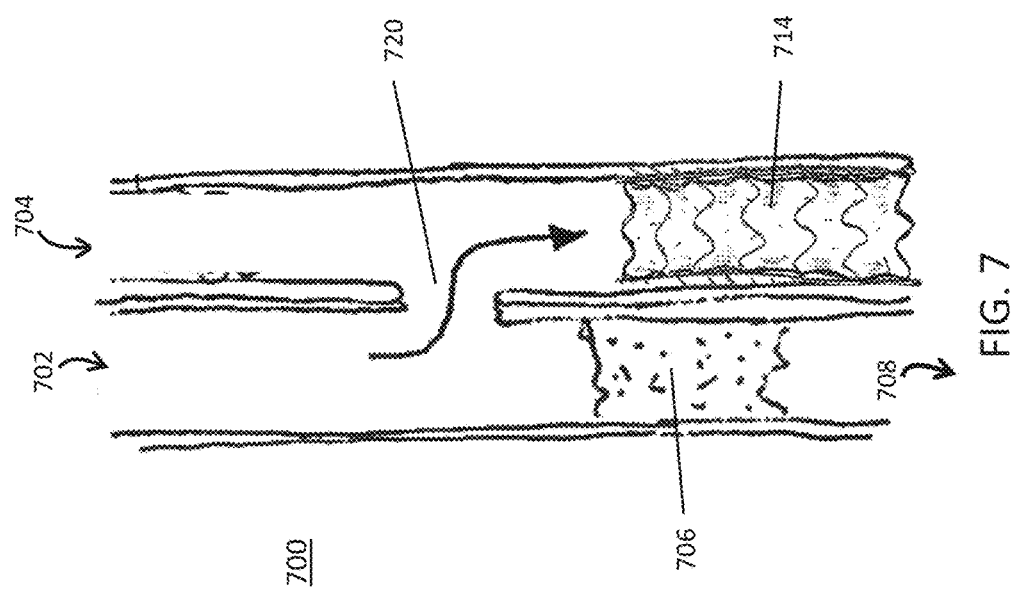

FIG. 7 shows an example diagram of vasculature (700) including an occlusion (706) in an artery (702) that forms a distal ischemia (708). The vasculature (700) is shown after a fistula (720) has been formed between the artery (702) and the vein (704) using the techniques described herein. Once the fistula (720) is formed, the venous valves distal to the fistula may limit retrograde blood flow. As shown in FIG. 7, in some variations a stent (714) may be deployed in a vein segment distal to the fistula to frustrate one or more venous valves without cutting them. This may allow blood to flow distally through the vein toward the distal ischemia.

Figure 8:
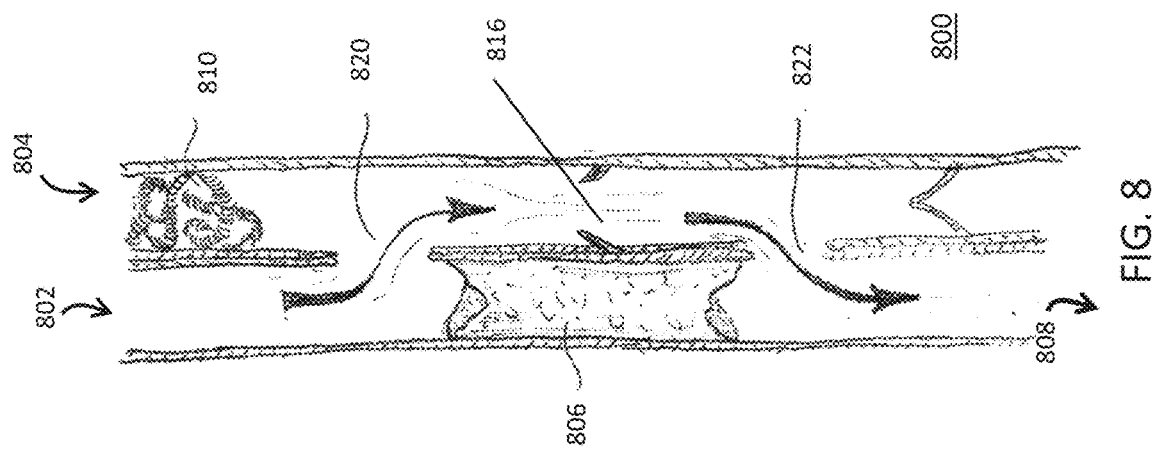
FIG. 7 and FIG. 8 each depict another variation of a method for perfusing ischemic tissue.

In some variations, two fistulas may be formed, with a first fistula located proximal to an occlusion and a second fistula located distal to an occlusion. FIG. 8 illustrates a variation of an arterial occlusion bypass providing flow diversion using venous segment arterialization for critical limb ischemia. As shown there, an arterial occlusion (806) may be bypassed by utilizing a venous segment to connect a portion of the artery (802) proximal to the occlusion (806) to a portion of the artery distal to the occlusion (806). Venous segment arterialization may thus provide distal arterial reperfusion of ischemic tissue (808). More particularly, FIG. 8 illustrates vasculature (800) including an occlusion (806) in an artery (802) that forms a distal ischemia (808). A first fistula (820) is formed proximal to the occlusion (806) between the artery (802) and vein (804). An embolization coil (810) may optionally be provided in the vein (804) proximal to the occlusion (806) and first fistula (820) to help drive arterial flow towards the lower extremities. Valves between the first fistula (820) and a site for a second fistula (822) may optionally be frustrated. For example, a valvulotomy may optionally be performed in the vein (804) between the first fistula (820) and a site for a second fistula (822), as shown in FIG. 8 with frustrated valve (816). As another example, a stent may be placed between the first fistula and second fistula site to hold the leaflets of the valve without cutting them In some variations, the first fistula (820) may be given time to mature prior to embolization and second fistula formation. This may allow the first fistula (820) to endothelialize prior to the pressurization caused by coiling. Next, the second fistula (822) may be formed between the artery (802) and vein (804) distal to the occlusion (806). Blood flowing back into the artery (802) from the vein (804) distal to the occlusion (806) may thus lead to distal arterial reperfusion. The fistulas may be formed as discussed herein.

Figure 9C:
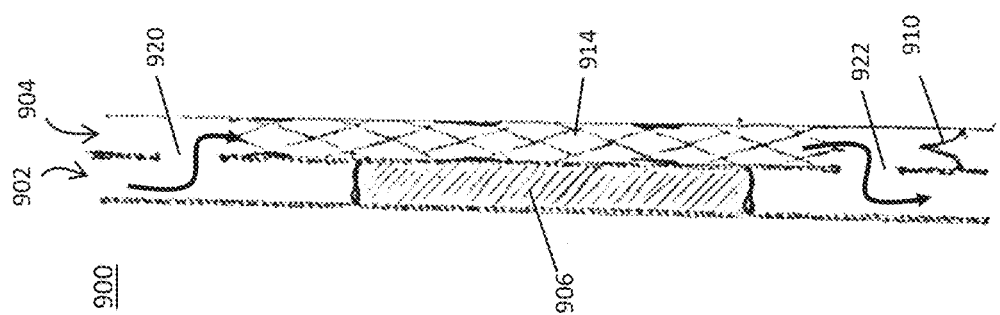
FIGS. 9A-9C depict a variation of a method for bypassing an occlusion using a stent.
Figure 9B:
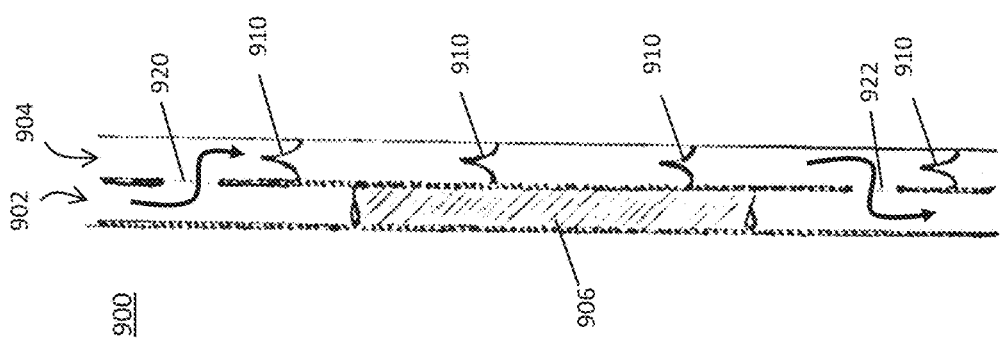
Figure 9A:
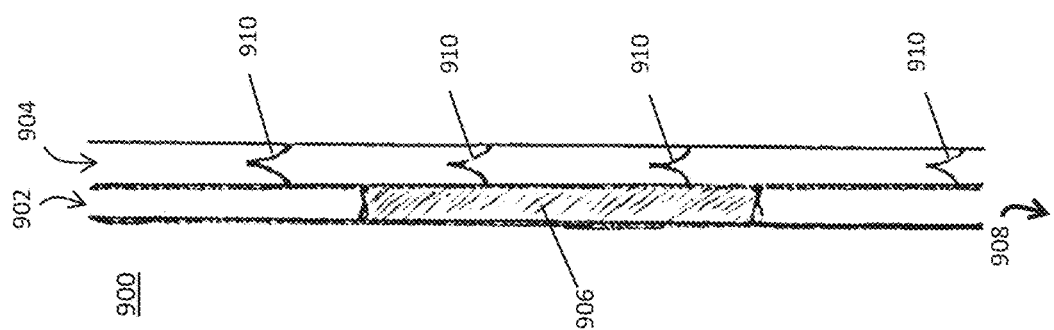

In some variations of methods in which fistulas are formed proximal and distal to an occlusion, one or more venous stents may be provided in a venous segment to improve perfusion of tissue distal to a fistula by allowing increased distal flow through the vein. For example, FIGS. 9A-9C illustrate a variation of an arterial occlusion bypass using a stent (914) in a segment of a vein (904) for increasing perfusion, e.g., for critical limb ischemia. As shown there, an arterial occlusion (906) may be bypassed by utilizing a portion of a vein to connect a portion of the artery (902) proximal to the occlusion (906) to a portion of the artery distal to the occlusion (906). Venous segment arterialization may thus provide distal arterial reperfusion of ischemic tissue. More particularly, FIG. 9A illustrates vasculature (900) having an occlusion (906) in an artery (902) that forms a distal ischemia (908). The vein (904) may comprise valves (910) concomitant to the occlusion (906) in the artery (902). As shown in FIG. 9B, a first fistula (920) may be formed between the artery (902) and vein (904) proximal to the occlusion (906), and a second fistula (922) may be formed between the artery (902) and vein (904) distal to the occlusion (906). It should be noted that an embolization coil and/or thrombogenic stent (not shown) may optionally be provided proximal to the occlusion (906) and first fistula (920) to help drive arterial flow towards the lower extremities, as discussed in more detail herein. In some variations, the first fistula (920) may be given time to mature (e.g., a day, a week, a month) prior to embolization and/or second fistula (922) formation. This may allow the first fistula (920) to stabilize or endothelialize prior to the increased pressurization caused by coiling and/or stenting. As shown in FIG. 9B, after formation of the first fistula, a second fistula (922) may be formed between the artery (902) and vein (904) distal to the occlusion (906). The fistulas may be formed as discussed herein.

As shown in FIG. 9C, a stent (914) may be deployed in the vein (904) over a plurality of venous valves between the first fistula (920) and the second fistula (922). The stent (914) may be configured to hold the leaflets of the valves in an open configuration along a length of the stent (914). This may provide a retrograde blood flow path in the vein (904) (e.g., from the first fistula (920) to the second fistula (922)) for blood to flow distally to perfuse distal ischemic tissue. FIG. 9C shows the stent (914) located proximal and distal to the occlusion (906). In some variations, the stent (914) when placed in the vein (904) may extend over the first fistula (920) and/or proximally to the first fistula (920), as discussed in more detail herein. Additionally or alternatively, the stent (914) may extend over the second fistula (922) and/or distally to the second fistula (922). It should be noted that a stent (914) extending over one or more of the first fistula (920) and second fistula (922) may not prevent blood flow through the fistula(s). For instance, the stent (914) may be porous to permit blood flow through one or more of the first fistula (920) and second fistula (922). For example, a stent comprising thin struts and wide apertures in a sidewall may permit greater blood flow through the stent (914). In some variations, in contrast, the stent may be configured to attenuate blood flow through a fistula. Although FIGS. 9B-9C show the formation of a second fistula (922) prior to delivering the stent (914) to the vein (904) (i.e., deploying the stent after formation of both fistulas), it should be appreciated that the stent (914) may be deployed in the vein (904) prior to formation of both the first fistula (920) or second fistula (922), or after formation of the first fistula (920) and prior to formation of the second fistula (922).

It should be appreciated that in some cases, use of a stent in venous tissue to frustrate one or more venous valves may be performed in fewer steps than a valvulotomy. A valvulotomy procedure to increase retrograde blood flow through a vein may require a user to visualize and locate a valve (e.g., using contrast), unsheath the valvulotome, cut the leaflets with the valvulotome, resheath the valvulotome, and repeat the process for each valve to be cut. This may be a time consuming process, as the location, size, and spacing of valves in peripheral vasculature varies per individual. By contrast, a venous stent having a length sufficient to cover a desired vein segment may be located and deployed once to hold a plurality of valves in an open configuration irrespective of the location, size, and spacing of the valves. Put another way, a venous stent may in some instances prevent valve function over a desired vein segment in fewer steps and less time than a valvulotome.

Figure 10:
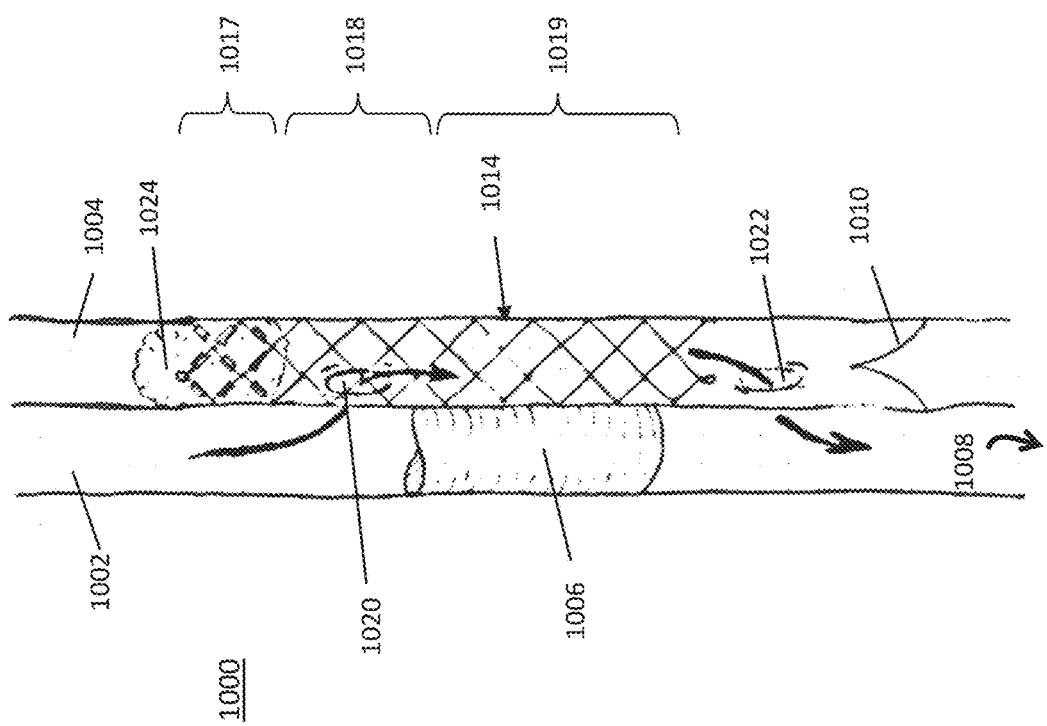
FIG. 10 depicts another variation of a method for bypassing an occlusion using a stent.

In some variations, a stent may be configured to additionally form a thrombus at a proximal end of the stent. For example, FIG. 10 shows another illustrative variation of an arterial occlusion bypass using a stent (1014) in a venous segment (1004) for increasing perfusion for critical limb ischemia. As shown there, an arterial occlusion (1006) may be bypassed by utilizing a venous segment to connect a portion of the artery (1002) proximal to the occlusion (1006) to a portion distal to the occlusion (1006). More particularly, FIG. 10 illustrates vasculature (1000) including an occlusion (1006) in an artery (1002) that forms a distal ischemia (1008). A first fistula (1020) may be formed proximal to the occlusion (1006) between the artery (1002) and vein (1004). A second fistula (1022) may be formed between the artery (1002) and vein (1004) distal to the occlusion (1006). A stent (1014) may be provided concomitant to the occlusion (1006) in a segment of the vein (1004).

The stent (1014) may comprise a thrombogenic proximal portion (1017), a distal portion (1019), and an intermediate portion (1018) disposed therebetween. The proximal portion (1017) of the stent (1014) may be delivered to a location within the vein (1004) proximal to the occlusion (1006) and first fistula (1020). In variations where the proximal portion (1017) of the stent (1014) comprises a thrombogenic material (1024), the proximal portion (1017) of the stent (1014) may form a thrombus proximal to a first fistula (1020) to help drive arterial blood flow towards the lower extremities. In some variations, the thrombogenic proximal portion (1017) may be configured to form a thrombus gradually at a predetermined rate (e.g., over a week). As opposed to immediate occlusion of the vein proximal to the first fistula (1020), gradual thrombus formation may slow the rate of pressurization of the first fistula (1020), thereby allowing the first fistula (1020) to mature as pressure increases. In contrast, immediate occlusion of a vein at a location proximal to the fistula may create a high blood flow rate and high pressure conditions in the fistula. The high pressure in the interstitial space may in turn increase the risk of fistula rupture. In some variations, a thrombus may be formed by a proximal portion (1017) of the stent (1014) in about a week, which is a slower rate than an embolization coil.

As one example, the proximal portion (1017) of the stent (1014) may comprise copper tubes crimped onto struts of the stent (1014) configured to induce thrombus and/or intimal hyperplasia over time (e.g., a week). In other variations, the proximal portion (1017) of the stent (1014) may be electroplated, comprise a coating for inducing thrombosis, and/or be made of a thrombogenic fiber. Alternatively, the proximal portion (1017) of the stent (1014) may comprise a semipermeable or impermeable membrane (e.g., cap, plug) to immediately reduce and/or eliminate proximal venous blood flow back to the heart.

The intermediate portion (1018) of the stent (1014) may be disposed over the first fistula (1020) and may be porous to permit blood flow from the first fistula (1020) to flow into the vein (1004). A distal portion (1019) of the stent (1014) may be configured to permit unobstructed blood flow through a lumen of the vein (1004) (e.g., by frustrating the venous valves). It may be desirable for the distal portion (1019) of the stent (1014) to have a minimal thickness and surface area necessary to hold open the venous valves. The stent (1014) may hold the venous valves in a vein segment in an open configuration. In particular, the distal portion (1019) of the stent (1014) may hold open the venous valves to increase retrograde blood flow through the vein (1004) without removing the valves. The distal portion (1019) may be placed proximal to the second fistula (1022) and be configured to prevent platelet aggregation and maximize retrograde blood flow through the vein (1004) toward the second fistula (1022). Blood may travel from the vein (1004) through the second fistula (1022) and back into the artery (1002). While shown as ending proximal to the second fistula (1022) in FIG. 10, it should be appreciated that in other variations, the stent (1014) may extend over the second fistula, and blood may flow through the stent wall.

Figure 11B:
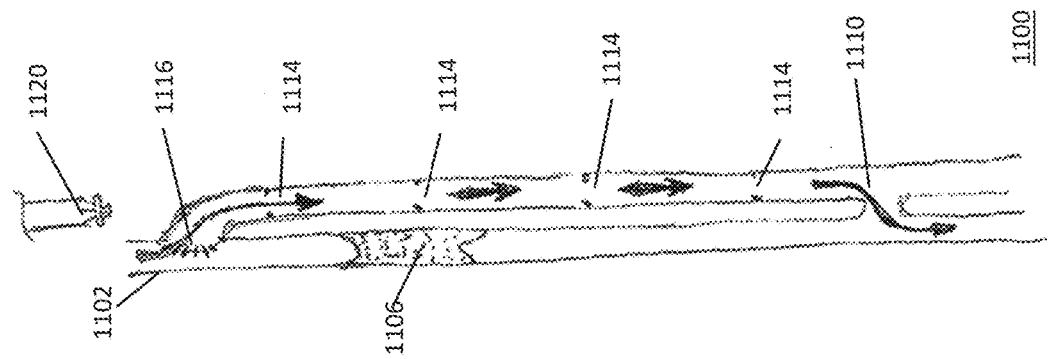
FIGS. 11A-11B depict a variation of a method for bypassing an occlusion.
Figure 11A:
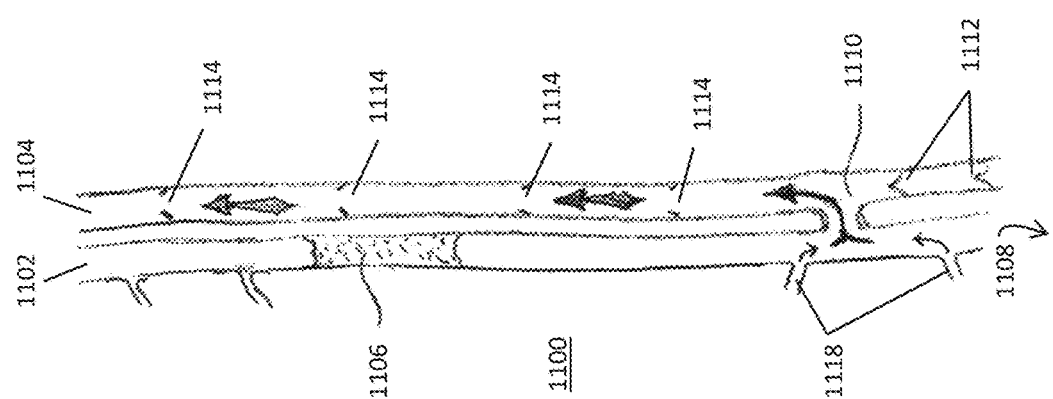

FIGS. 11A-11B illustrate another method for bypassing an occlusion (1106) in vasculature (1100). FIG. 11A illustrates vasculature (1100) including an occlusion (1106) in an artery (1102) that forms a distal ischemia (1108). A fistula (1110) may be formed distal to the occlusion (1106) in a manner as described herein. A valvulotomy may be performed at or near the time of fistula formation to render valves (1114) proximal to the fistula (1110) incompetent. Additionally or alternatively, a stent of a predetermined length may be provided in the vein (1104) proximal to the fistula (1110) to render the valves (1114) incompetent. Although arterial blood flow distal to the occlusion (1106) may be limited due to the occlusion (1106), arterial blood from the collateral arteries (1118) may feed the fistula (1110) to arterialize the vein (1104). Vein arterialization may occur in about 1-2 months.

As shown in FIG. 11B, to create the arterial occlusion bypass (1106), a proximal anastomosis (1116) of the vein (1104) and artery (1102) may be created to allow arterial blood flow to travel distally through the arterialized vein segment and back into the artery (1102) through the first fistula (1110). For example, the proximal anastomosis may be formed between the femoral artery, popliteal artery, or tibial artery adjacent to the arterialized vein. In order to push arterial flow unidirectionally distally, embolization (e.g., using coils or plugs) or surgical ligature (1120) may be performed on a section of the vein (1104) proximal to the anastomosis. Venous outflow may thus be reversed in the venous segment. Alternatively, a side-to-side anastomosis may be performed with a proximal coil. In this way, distal perfusion may be achieved.

FIG. 12 is a diagram of an in situ femoral-popliteal occlusion bypass in the femoral artery (1210) using percutaneous fistulas (1218, 1220) that arterialize a concomitant vein segment around the occlusion (1216). FIG. 12 shows vasculature (1200) including a common iliac artery (1202) feeding a femoral artery (1210). The external iliac artery (1206) branches from the common iliac artery (1202). The femoral profunda (1208) branches from the femoral artery (1210). An occlusion (1216) is located in the femoral artery (1210). The femoral vein (1214) connects to the greater saphenous vein (1212) and feeds into the common iliac vein (1204).

In some variations of an arterial obstruction bypass, the femoral artery (1210) may be accessed distal to the occlusion (1216). For example, the femoral artery (1210) may be accessed through the anterior dorsalis pedis artery, the anterior tibial artery, the posterior tibial artery, the peroneal artery, etc. The femoral artery (1210) may also be accessed proximal to the occlusion (1216). The femoral vein (1214) may also be accessed proximally or distally to the occlusion (1216). A first catheter may be advanced through the distal arterial access to a location distal to the occlusion (1216). A second catheter may be advanced through the first venous access to a location distal to the first fistula site. After advancement of the catheters, the catheters may be axially and/or rotationally aligned so as to coapt a segment of the femoral artery (1210) to the femoral vein (1214). The catheters may then be used to form a fistula (1220). For example, once a fistula-forming element (e.g., electrode) is deployed or otherwise in position to ablate tissue, radiofrequency energy may be applied to create the fistula. In some variations, an electrode on the venous catheter may additionally or alternatively be used to ablate tissue to create the fistula. Fistula formation may be confirmed through angiography or other methods. The catheters may then be removed after formation of the first fistula (1220). In some variations, the fistula may be allowed to mature and heal prior to proceeding with the next steps. The maturation time may be up to about 2 months.

After creation of the first fistula (1220), a first catheter may be advanced through the second arterial access to a second fistula formation site proximal to the occlusion (1216). After maturation of the fistula and vein, an artery may be accessed in an antegrade or contralateral approach from the femoral artery (1210). A second catheter may be advanced or retracted through the femoral vein (1214) to the second fistula formation site. The first and second catheters may be positioned and aligned at the second fistula formation site. More particularly, the first and second catheters may be axially and rotationally aligned, for example using magnets located within the catheters, which may coapt a segment of the artery to the vein. After alignment, tissue may be ablated to create the second fistula (1218) using the catheters, as described herein. The first and second catheters may then be removed from the body. The bypass flow may be confirmed visually through angiography or other methods. Access sheaths may be removed and hemostasis may be achieved using manual compression. Alternatively, instead of creating a second proximal fistula (1218), a proximal surgical anastomosis may be created, and the venous valves may be rendered incompetent (e.g., valvulotomy may be performed, or a stent may be placed in the vein segment).

In some variations, a valvulotomy may be performed on venous valves in the vein segment between the first and second fistulas (1218, 1220) to increase retrograde flow and prevent back up through the femoral vein (1214). In some variations, the valvulotomy may be performed by inserting a valvulotome through the venous access. Additionally or alternatively, a venous catheter may be advanced to a location proximal to the second fistula (1218). The venous catheter may then deploy one or more embolization coils (1222) to restrict or eliminate antegrade flow in the vein (1214). However, coil embolizing the femoral vein (1214)

may also reduce venous return of blood from the lower extremities to the heart. To compensate, a valvulotomy may be performed to frustrate one or more valves in the perforator veins (1226) that connect the femoral vein (1214) to the greater saphenous vein (1212). These perforator valves typically allow unidirectional flow from the superficial saphenous vein to the deep femoral vein, which is to say from the superficial system to the deep system. By frustrating the perforator valves (1224) distal to competent femoral vein valves that are distal to the arterialized femoral vein segment, femoral vein flow from the lower extremities may be shunted to the lower pressure saphenous vein (1212) and return to the iliac vein (1204) at the proximal femoral-saphenous anastomoses. This may provide a significant venous return pathway that may compensate for the obstructed flow created by the embolization coil (1222), or by a plug. When the coil embolization (1222) of the femoral vein (1214) lies distal to the saphenous-femoral anastomosis, venous return may be maintained for adequate drainage from the limb towards the heart. Additionally or alternatively, a stent may be provided in one or more of the femoral vein (1214) and/or perforator veins (1226). A thrombogenic stent may be deployed in the femoral vein (1214) in place of the embolization coil (1222) to restrict or eliminate antegrade flow in the vein (1214) over a predetermined period of time.

In some variations, the first and second fistulas (1220, 1218) may be formed in a single procedure. A single procedure may be used, for example, when the femoral vein (1214) is free of obstructions proximal to the second fistula (1218). The fistulas may then mature, heal, and seal under low pressure to prevent extravasation. At the time of a second intervention, an embolization coil (1222) and/or thrombogenic stent may be deployed just proximal to the second fistula (1218). The femoral vein valves may then be excised, thereby reversing the direction of blood flow.

FIG. 13 depicts a variation of a fluid flow schematic after completion of a bypass procedure. As shown there, an occlusion (1306) in a femoral artery (1302) may create a distal ischemic tissue (1308). A first fistula (1316) may be formed between the femoral artery (1302) and a femoral vein (1304) distal to the occlusion (1306), and a second fistula (1310) may be formed between the femoral artery (1302) and a femoral vein (1304) proximal to the occlusion (1306). The first and second fistulas (1316, 1310) may provide arterialized flow through a segment of the femoral vein (1304) and back into the distal ischemic tissue (1308). In some variations, an artificial occlusion (1312) such as a plug, embolization coil, or thrombogenic stent may be placed in the femoral vein (1304) proximal to the second fistula (1310) to prevent arterialized vein flow from the second fistula (1310) from returning directly to the central venous system.

Before or after fistula formation, a valvulotomy may be performed on femoral vein valves (1326) between the first and second fistulas (1316, 1310) to provide an unobstructed fluid flow path to distal ischemic tissue (1308). For example, a valvulotome may be advanced through a venous access and used to reduce back flow through the first fistula (1316). Additionally or alternatively, a stent may be provided between the first and second fistulas (1316, 1310) to hold the femoral vein valves (1326) in an open configuration.

As shown, a set of perforator veins (1318) connect the femoral vein (1304) to the greater saphenous vein (1320). A valvulotomy may be performed to frustrate one or more perforator valves (1314) in one or more perforator veins (1318) to allow femoral vein flow distal to the first fistula (1316) to flow into the greater saphenous vein (1320). Additionally or alternatively, a stent may be provided in one or more perforator veins (1318) to hold the perforator valves (1314) in an open configuration. A plurality of perforator valves (1314) may be frustrated to increase flow from a deep venous system to the superficial venous system. A set of competent perforator valves (1324) between the first and second fistulas (1316, 1310) may be left intact to prevent arterial flow in the femoral vein (1304) from shunting into the greater saphenous vein (1320). The greater saphenous vein (1320) connects with the femoral vein (1304) proximal to the second fistula (1310) and the plug/coil/stent (1312) to return venous blood flow to the central venous system.

B. Venous Flow

Generally, the devices, systems, and methods described here may also be used to form a fistula to increase fluid flow through a stent graft in a vein, such as an iliac vein. In some variations, the fistula may arterialize the stented venous segment to improve graft patency of a venous stent graft. In one variation, an arteriovenous fistula is formed between the deep femoral artery (e.g., profunda femoris) and an adjacent vein that feeds the deep venous system. Arterialized flow may thus flow through a stented venous segment and may prevent post-venous stenting acute thrombosis.

FIG. 14 is a diagram of a fistula (1408) formed between an artery (1402) and vein (1404) distal to a venous stent graft (1406). The artery (1402) may be, for example a deep femoral artery (1402) and the vein (1404) may be an adjacent vein. An artery (1402) may be accessed distal or proximal to the venous stent graft (1406), and the vein (1404) may be accessed distal or proximal to the venous stent graft (1406). A first catheter may be advanced through the artery (1402) and a second catheter may be advanced through the vein (1404) to a location distal to the venous stent graft (1406). After advancement, the catheters may be axially and rotationally aligned so as to coapt a segment of the artery (1402) and vein (1404). Once a fistula-forming element (e.g., electrode) is deployed or otherwise in position to ablate tissue, the fistula-forming element may be used to form a fistula (1408) (e.g., radiofrequency energy may be applied to create the fistula). In some variations, a venous catheter electrode may ablate the tissue to create the fistula (1408). The catheters may be removed after formation of the fistula (1408). Fistula formation may be confirmed such as through angiography or other methods. Access sheaths may be removed, and hemostasis may be achieved using compression.

After fistula formation, venous blood flow that typically returns through a femoral vein (1404) may be obstructed by the arterialization of the vein (1404) caused by the fistula (1408). In order to provide a significant return pathway for venous blood, a valvulotomy may be performed on perforator valves (not shown) in the perforator veins that connect the femoral vein (1404) to a saphenous vein. Additionally or alternatively, a stent may be provided in one or more perforator veins to hold the perforator valves in an open configuration. These valves typically allow unidirectional flow from the saphenous vein to the femoral vein (e.g., superficial venous system to deep venous system). By frustrating the perforator valves distal to competent femoral vein valves that are distal to the arterialized femoral vein segment, distal femoral vein flow may be shunted to the low pressure saphenous vein and may return to the iliac vein at the proximal femoral-saphenous anastomoses or through branching collaterals.

Although the foregoing variations have, for the purposes of clarity and understanding, been described in some detail by of illustration and example, it will be apparent that certain changes and modifications may be practiced, and are intended to fall within the scope of the appended claims. Additionally, it should be understood that the components and characteristics of the devices and methods described herein may be used in any appropriate combination. The description of certain elements or characteristics with respect to a specific figure are not intended to be limiting or nor should they be interpreted to suggest that the element cannot be used in combination with any of the other described elements.

We claim:

1. A method for improving blood flow in a vessel comprising:
    advancing a first catheter into a first vessel proximal to and upstream of an occlusion in the first vessel, wherein the first catheter comprises a fistula-forming element;
    advancing a second catheter into a second vessel, wherein the second vessel is adjacent to the first vessel; and
    forming a fistula between the first vessel and the second vessel using the fistula-forming element at a position upstream of the occlusion, wherein the fistula allows blood to flow past the occlusion through the second vessel.

2. The method of claim 1, wherein the fistula-forming element comprises an electrode.

3. The method of claim 1, wherein each of the first and second catheters comprises a magnet.

4. The method of claim 1, further comprising providing an embolization coil in the second vessel.

5. The method of claim 4, wherein the embolization coil is located proximal to the occlusion.

6. The method of claim 1, further comprising performing a valvulotomy in the second vessel.

7. The method of claim 6, wherein the valvulotomy is performed distal to the fistula.

8. The method of claim 1, wherein the first vessel is an artery and the second vessel is a vein.

9. The method of claim 1, further comprising advancing a third catheter comprising a second fistula-forming element into the first vessel distal to the occlusion in the first vessel, advancing a fourth catheter into the second vessel, and forming a second fistula between the first vessel and the second vessel using the second fistula-forming element.

10. The method of claim 9, wherein the second fistula-forming element comprises an electrode.

11. The method of claim 9, further comprising deploying a stent in the second vessel, and wherein the stent extends over both the first and second fistulas.

12. The method of claim 1, wherein the first vessel is the femoral artery.

13. The method of claim 12, wherein the second vessel is the femoral vein.

14. The method of claim 1, wherein the second vessel contains a stent graft.

15. The method of claim 1, further comprising deploying a stent over one or more valves in the second vessel.

16. The method of claim 15, wherein the stent holds the one or more valves in an open configuration.

17. The method of claim 15, wherein the stent is deployed proximal to the occlusion.

18. The method of claim 17, wherein the stent is deployed proximal to the fistula.

19. The method of claim 18, wherein the stent is deployed over the fistula.

20. The method of claim 15, further comprising forming a thrombosis at a proximal portion of the stent.

21. The method of claim 20, wherein the thrombosis is formed at a predetermined rate.

* * * * *